(12) United States Patent
Felber

(10) Patent No.: US 12,427,258 B2
(45) Date of Patent: Sep. 30, 2025

(54) SELF-INJECTOR

(71) Applicant: BIOREM AG, Baar (CH)

(72) Inventor: Josef Felber, Zollikon (CH)

(73) Assignee: BIOREM AG, Baar (CH)

(*) Notice: Subject to any disclaimer, the term of this patent is extended or adjusted under 35 U.S.C. 154(b) by 0 days.

(21) Appl. No.: 18/872,724

(22) PCT Filed: Jun. 9, 2023

(86) PCT No.: PCT/EP2023/065437
§ 371 (c)(1),
(2) Date: Dec. 6, 2024

(87) PCT Pub. No.: WO2023/237711
PCT Pub. Date: Dec. 14, 2023

(65) Prior Publication Data
US 2025/0161570 A1    May 22, 2025

(30) Foreign Application Priority Data
Jun. 9, 2022   (CH) ................................ 000704/2022

(51) Int. Cl.
*A61M 5/20*      (2006.01)
*A61M 5/32*      (2006.01)

(52) U.S. Cl.
CPC ........ *A61M 5/2033* (2013.01); *A61M 5/2053* (2013.01); *A61M 5/3234* (2013.01);
(Continued)

(58) Field of Classification Search
CPC .............. A61M 5/2033; A61M 5/2053; A61M 5/3234; A61M 2005/2013;
(Continued)

(56) References Cited

U.S. PATENT DOCUMENTS 5,865,804 A * 2/1999 Bachynsky ......... A61M 5/2033
604/233
9,242,045 B2 * 1/2016 Burnell ............... A61M 5/2033
(Continued)

FOREIGN PATENT DOCUMENTS

WO   WO 2009/098502 A2   8/2009
WO   WO 2016/091869 A1   6/2016

*Primary Examiner* — Michael J Tsai
*Assistant Examiner* — Neeraja Gollamudi
(74) *Attorney, Agent, or Firm* — Straylight LLP

(57) ABSTRACT

The auto-injector contains a torsion spring with stored energy for administration of a liquid active substance. It has a housing with a holder for securing an insertable syringe with barrel, sealing plug and needle, the active substance of which it can discharge hydraulically when triggered to do so. The piston in the barrel can be actuated by a pivot lever articulated on a piston slide guided along a rail in the housing. The other end of the pivot lever is articulated on a pivotable leg of a biased torsion spring. By means of the triggered pivoting movement of the biased spring leg, the piston can slide into the syringe in a pivoting phase with a piston slide, and a barb on the piston slide can latch onto the syringe. In a subsequent pivoting movement, the syringe can be retracted into the housing, such that the needle disappears in the housing.

11 Claims, 20 Drawing Sheets

(52) U.S. Cl.
CPC .............. *A61M 2005/2013* (2013.01); *A61M 2005/202* (2013.01); *A61M 2005/206* (2013.01); *A61M 2005/3236* (2013.01)

(58) Field of Classification Search
CPC ...... A61M 2005/202; A61M 2005/206; A61M 2005/3236; A61M 5/1454; A61M 5/178; A61M 5/31511; A61M 5/31515
See application file for complete search history.

(56) References Cited

U.S. PATENT DOCUMENTS

| | | | | |
|---|---|---|---|---|
| 2003/0105430 | A1* | 6/2003 | Lavi | A61M 5/2033 604/890.1 |
| 2013/0331771 | A1* | 12/2013 | Kirk | A61M 5/19 604/24 |
| 2018/0200442 | A1* | 7/2018 | Atterbury | A61M 5/3287 |

* cited by examiner

023
SELF-INJECTOR

TECHNICAL FIELD

The present invention relates to a self-injector for administering medicaments by injection by the user himself.

BACKGROUND

Almost half of all medicines today are administered by syringe. This corresponds to around 50 billion syringe applications worldwide every year. A third of these are administered orally, the rest rectally or via the eyes, nose and ears. Insulin accounts for the largest proportion of self-injections. An autoinjector used for this purpose contains stored energy for injecting the liquid medication. The growth of the market for such prefilled syringes is mainly driven by the increasing demand for prefilled syringes due to the growing prevalence of chronic diseases, technological advancements, increasing adoption of self-injecting parenteral devices, and supportive government regulations (especially needle stick laws). In addition, the growth of the prefilled syringes market is supported by the growing awareness of the benefits of prefilled syringes among patients and healthcare professionals and the increasing number of biologics and biosimilars in the pharmaceutical market.

For example, a device for administering medication is known from WO 2011043714 A1. This comprises an elongate tubular housing with opposing proximal 10 and distal 12 parts. Further, a needle protection sleeve 20 is provided, which is slidably and coaxially arranged within the housing. A syringe carrier mechanism comprises a syringe carrier 36 which is slidably arranged within the needle protection sleeve. The syringe 16 includes a stopper 92, a medicament and a needle and is disposed within the syringe carrier. A first activator element 56 is slidably disposed within the housing and connected to the needle protection sleeve. A second activator element 66 is slidably disposed within the first activator element. Further, there is a drive mechanism slidably disposed within the second drive mechanism, which in turn is slidably disposed within the second activator element and releasably connected to the retaining element and the second activator element. This drive mechanism can develop a driving force to move the syringe carrier mechanism in a first step to insert the needle into an injection site and to move the stopper in a second step to eject the medicament through the needle. For this purpose, the drive mechanism is controlled by the first and second activation elements. This device has, as a special feature, a second activator element 66 having information means such that, after the medicament is completely ejected, a remaining driving force forces the second activator element to be displaced towards the distal portion of the elongated tubular housing to provide an audible, visual and/or tactile feedback to a user of a completed injection.

Further known from US 1 0420 898 is a medication dispensing device with a drive means configured to act on a medication container to eject a medication. For this purpose, it has a holding means configured to hold the drive means in a preloaded state. Further, there is activation means cooperating to cooperate with the holding means to release the drive means from the biased state, the device further comprising feedback means configured to cooperate with both the holding means and drive means to produce an audible and/or tactile and/or visual signal indicating that the medicament has been fully ejected. US-A-20040054326 describes, in particular as shown in FIGS. 1-5, an autoinjector comprising a body portion 21 for receiving a syringe or cartridge 1 having a bung slidably mounted therein with a bung slidably mounted therein for ejecting a dose; a drive mechanism including energy storage means 10 in the form of a coil spring and adapted to cause ejection of a dose upon actuation of a trigger 14 from a cocked position, the drive mechanism comprising a rotatable crank mechanism 8 associated with a slidable drive piston 5 and the spiral spring acts on a rotary cam element 8. However, the force that can be applied and the force progression is too weak when driven by a spiral spring and complete emptying of the inserted syringe can hardly be guaranteed.

In view of this prior art, the object of the present invention is to provide an improved self-injector which is less expensive to manufacture and offers a high degree of functional safety, so that the safe administration of a liquid medication is provided, and which consists of fewer parts than conventional solutions, with a minimum proportion of parts made of metal, and which is easy and foolproof for the user to handle. In particular, it is also designed to safely prevent injury or infection with the used syringe needle and to retract the needle of the syringe completely into the housing after activation so that it cannot injure or infect anyone.

The solution provides a self-injector with stored energy for the application of a contained liquid active substance with a housing, a holder for holding a syringe to be inserted with cylinder, sealing pin and needle, for hydraulic ejection of the active substance through the needle, which is characterized in that the piston can be actuated by a piston slide guided along a rail in the housing by a swivel lever articulated to the same, and the other end of the pivot lever is articulated to a pivotable spring leg of a prestressed torsion spring with a plurality of coils, the second spring leg being stationarily locked on the housing, and the pivoting movement of the pivotable spring leg can be triggered by releasing the prestressed torsion spring, wherein, in a first pivoting phase, the piston can be pushed into the syringe with the pivoting spring leg and the piston slide articulated at its end, and thus a barb on the piston slide can be latched onto the syringe, and then, in a subsequent pivoting phase, the piston can be pushed into the syringe with the piston slide articulated at its end.

BRIEF DESCRIPTION OF THE FIGURES

An embodiment example of this self-injector is described in detail below with reference to the figures and its function is explained.

It shows.

DETAILED DESCRIPTION

Figure 1:
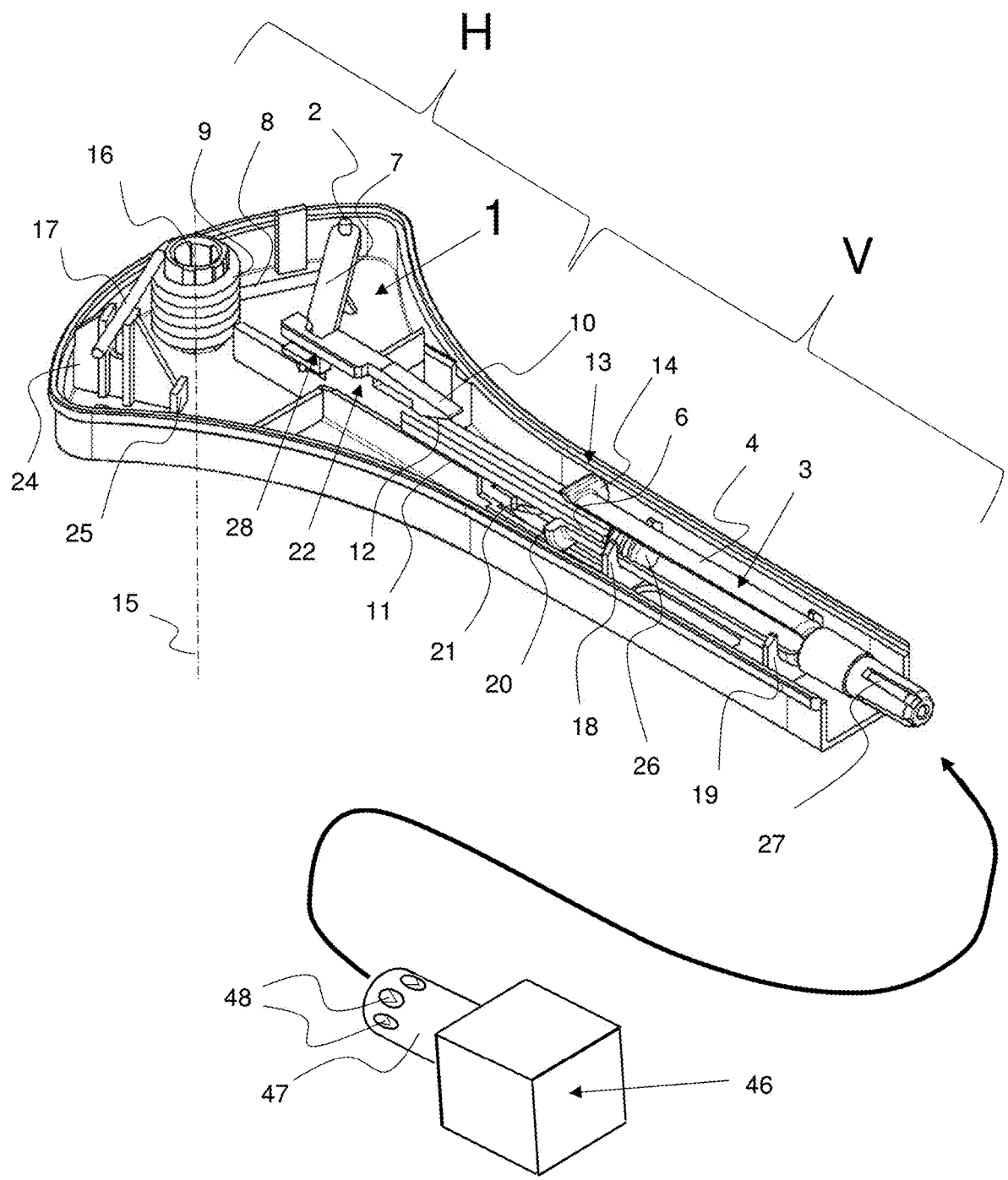
FIG. 1: A self-injector with its lower housing part after removal of the upper housing part, with all components located therein, with the push-on cap on the needle and the associated puller for removing the push-on cap.

FIG. 1 shows the self-injector with its lower housing part 1 after removal of the upper housing part, with all components located therein, with a push-on cap 27 on the needle, which is therefore not visible here. In the following, all parts or components of this self-injector are first designated and described. The rear housing part H contains the entire drive mechanism for the self-injector. At the rear of the housing 1 is a bolt 16 in the form of a hollow cylinder injection-moulded from plastic, on which a torsion spring 9 is mounted. The axis 15 of the torsion spring 9 is marked and runs perpendicular to the base of the housing. One spring leg 17 of this torsion spring 9 is mounted stationary and strikes the housing 1 and is held in a correspondingly shaped retainer 24 for this purpose. The other spring leg 8 is movable and is connected at its outer end to the rear end of a swivel lever 7 via the knee joint 2. The movable spring leg 8 can pivot clockwise from this starting position shown in the picture by virtue of the torsion spring 9 until it strikes the limiting cam 25. As a result, it also swivels the swivel lever 7 from the starting position shown here in relation to the longitudinal axis of the housing 1 into an approximately symmetrically opposite position. At the same time, the swivel lever 7 pushes the piston slide 22 connected to it via a joint 28 from the rear to the front, i.e. in the direction where the syringe 3 is located, until the swivel lever 7 runs in the same direction as the piston slide 22, and at the Further pivoting pulls the plunger slide 22 back a little until the movable spring leg 8 strikes the limiting cam 25. Before use, the needle of the syringe protrudes from the front of the housing 1 and is protected by a rubber or plastic push-on cap 27, which is why it is not visible here. It is completely enclosed by a cubic or rectangular protective chamber 35 with a hole 37 at the front, whereby this protective chamber is only shown from FIG. 22 onwards. It serves on the one hand as protection for the needle and on the other hand for triggering the self-injector, as will become clear later. A puller 46 is also shown at the bottom. Such a puller 46 for the push-on cap 27 is placed on the push-on cap 27 and over the protective chamber 35, an approximately cubic or rectangular plastic hollow body with an open side, from which a metal tube section 47 with inwardly projecting barbs 48 protrudes. This extractor 46 is slipped over the push-on cap 27 from the front with its tube section 47, so that the self-injector is delivered with the syringe fitted with this cubic extractor 46 and, in the as-delivered state, it connects directly to the protective chamber 35 not yet shown here. The housing therefore ends at the front with this cubic or rectangular closed end, namely with this puller 46. To use the syringe 3, the user only needs to remove the push-on cap 27 by pulling this puller 46 away from the housing 1, and its barbs 48 pull the push-on cap 27 securely away from the needle. Even then, however, the needle is still protected inside a protective chamber 35 with a hole 37 at the front. This protective cap 35 is part of the release mechanism and is shown and described from FIG. 22 onwards. The user can press this protective chamber 35 with its hole 37 directly against his body at the desired location. When the self-injector is pressed onto the skin, the protective chamber 35 is pushed a little way into the housing 1 and thus triggers the injection. The active ingredient is then injected automatically and the needle is immediately and automatically withdrawn into the housing 1 so that it disappears completely and can no longer injure or infect anyone.

The piston slide 22 is integrally formed at the front end in the form of a piston 6, which plunges into the open end of the cylinder 4 of the syringe 3, which is inserted into the front housing part V, and this piston slide 22 is arranged along a rail 11, which forms a groove, is guided on the housing 1 so that it can be moved longitudinally. The syringe 3 rests on a holder in the housing 1, here in the form of two U-shaped bars 18, 19, into which the syringe 3 with its cylinder 4 fits. A sealing pin 26 can be seen at the front of the plunger 6, which is located inside the cylinder 4 can be pushed forward in a sealing manner, for hydraulic ejection of the syringe contents from the front of the needle. An elastic barb 10 is formed on the plunger slide 22, with a push-on ramp 12 on its underside, with which it can move over the rear end 13 of the syringe 3 and then hook onto the flange 14 of the syringe 3 in order to pull it back into the housing 1 after injection has been completed. However, to prevent the syringe 3 from being pushed backwards in the housing 1 when the needle is inserted, a stop 20 for the flange 14 is formed in the housing base 1. At the rear, adjacent to this stop 20, there is a ramp 21 that slopes downwards towards the rear or upwards towards the front. If the plunger slide 22 is moved forwards, its lower edge, which also forms a ramp not visible here, moves onto this ramp 21 at the end and presses the elastic leg 29 downwards, whereby the stop 20 releases the flange 14 so that the syringe 3 can be pulled into the housing unhindered by the barb 10.

In the following, the function of this self-injector is shown, described and explained step by step, using chronological image sequences which initially show the lower part of the housing and the internal parts except for the release mechanism.

Figure 2:
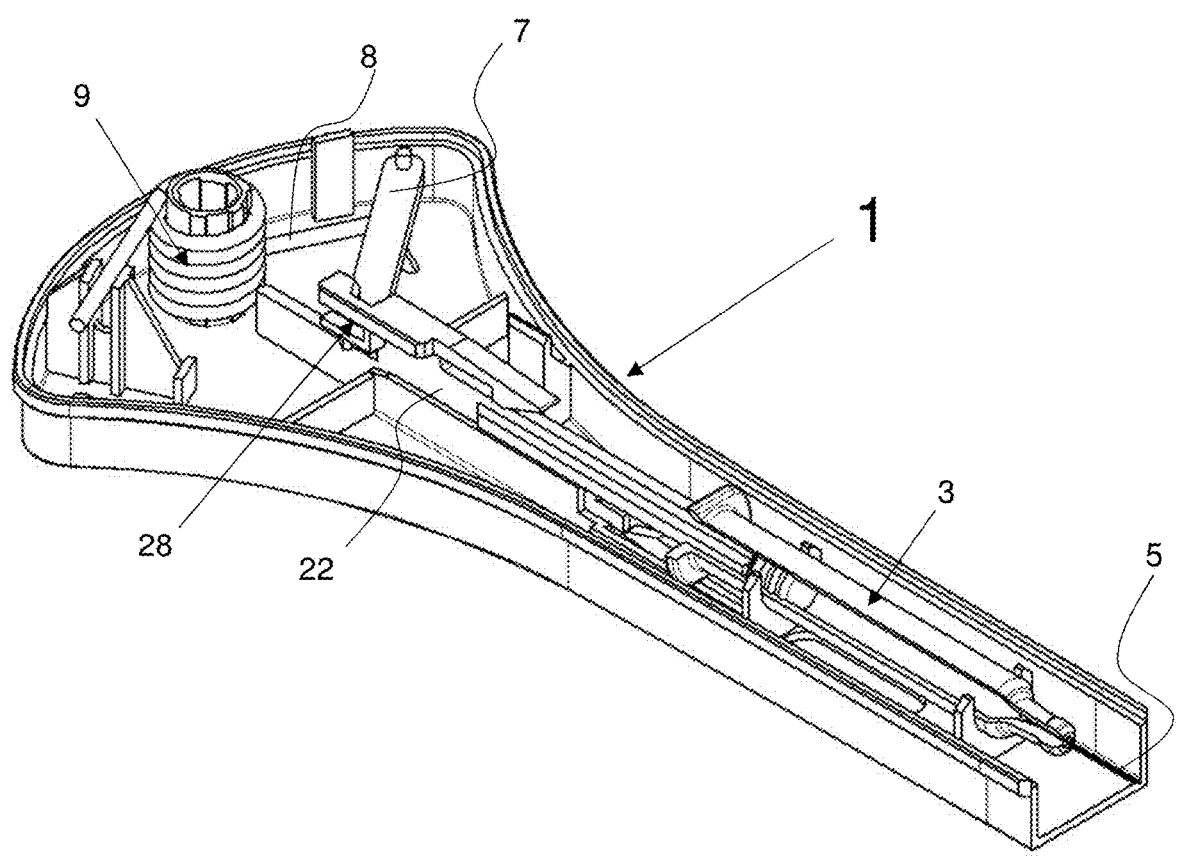
FIG. 2: This self-injector with all internal components after removal of the push-on cap from the needle, in the constellation of the drive means ready for injection.

To this end, FIG. 2 shows the self-injector after removal of the push-on cap

27 so that the needle 5 is now visible. In this constellation of the drive mechanism, the self-injector is ready to inject the active ingredient contained in the syringe 3. The torsion spring 9 is tensioned, i.e. its movable spring leg 8 is in the pretensioned position shown here and is secured in the same position because the piston slide 22 is locked by a releasable pawl, as this release mechanism is described in detail in FIG. 22 *ff*. For use, the user presses the protective chamber 35, not shown here, onto the body at the desired position. It is pushed a little way into the housing 1 and the needle 5 penetrates the skin and at the same time the injection is triggered, as will be described later. After triggering, the movable spring leg 8 starts its swivel movement, which causes the injection. The syringe 3 together with the needle 5 is then automatically retracted into the housing so that the needle 5 disappears into the housing 1 and cannot injure or infect anyone.

Figure 3:
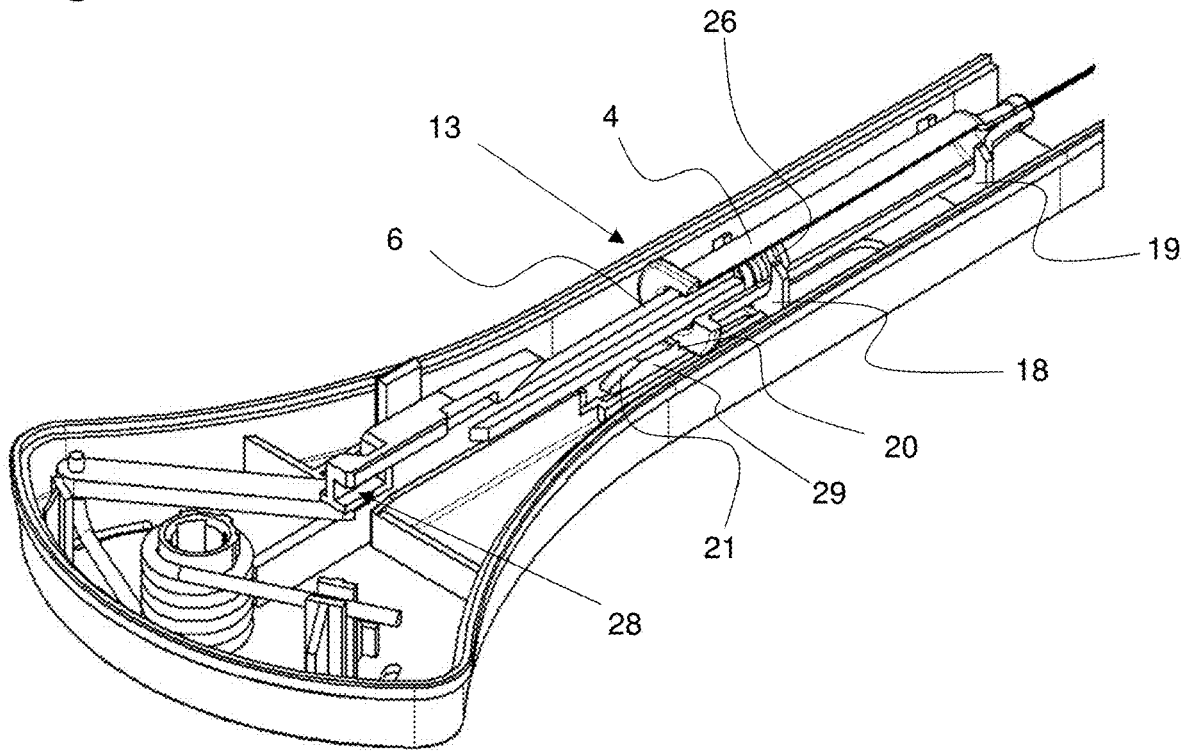
FIG. 3: This self-injector according to FIG. 2 seen from the rear.

FIG. 3 shows this self-injector in the position shown in FIG. 2, viewed from the other, rear side. The holders for the syringe can be seen here, namely the bars 18, 19 cut out in a U-shape at the top, on which the inserted syringe 3 rests with its cylinder 4. You can also see the stop 20, which prevents the syringe 3 from being pushed further backwards into the housing 1, and the drive-on ramp 21, which is formed on a leg 29, which is rooted in the housing base, and onto which the plunger slide 22 can be driven to release the rear end of the syringe 13.

Figure 4:
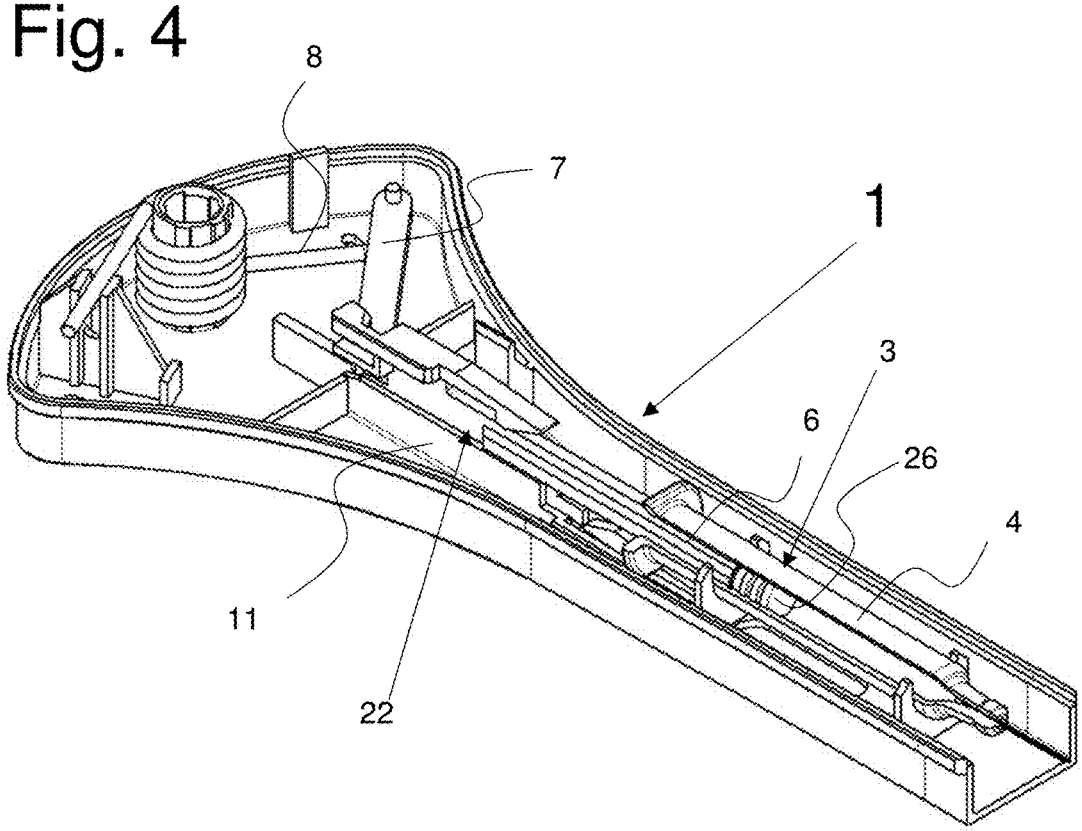
FIG. 4: This self-injector with all internal components shortly after initiating an injection, with the plunger slightly retracted into the syringe barrel.
Figure 5:
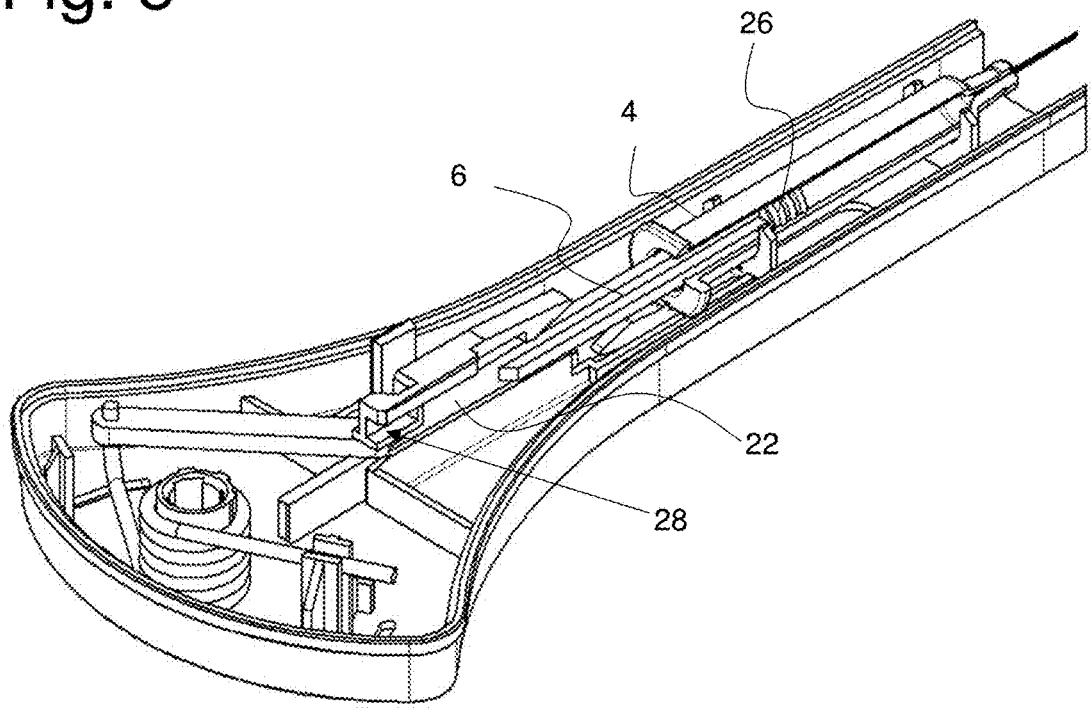
FIG. 5: This self-injector according to FIG. 4 seen from the rear.

In FIG. 4, the self-injector is shown shortly after the initiation of an injection, with the plunger 6 already slightly retracted into the syringe cylinder 4. As can be seen, the movable spring leg 8 has traveled some distance and thus pushed the lever 7, which is articulated with its front end to the plunger slide 22 via the joint 28, forward along the rail 11 for the plunger slide 22. The front end of the piston 6 is inserted into the cylinder 4 of the syringe 3 and pushes the sealing pin 26 forwards. Accordingly, active substance is injected from the inside of the cylinder 4 through the needle 5. FIG. 5 shows the self-injector in the position shown in FIG. 4, viewed from the other, rear side. The sealing pin 26 is located in front of the front end of the piston 6 in the cylinder 4 of the syringe 3.

Figure 6:
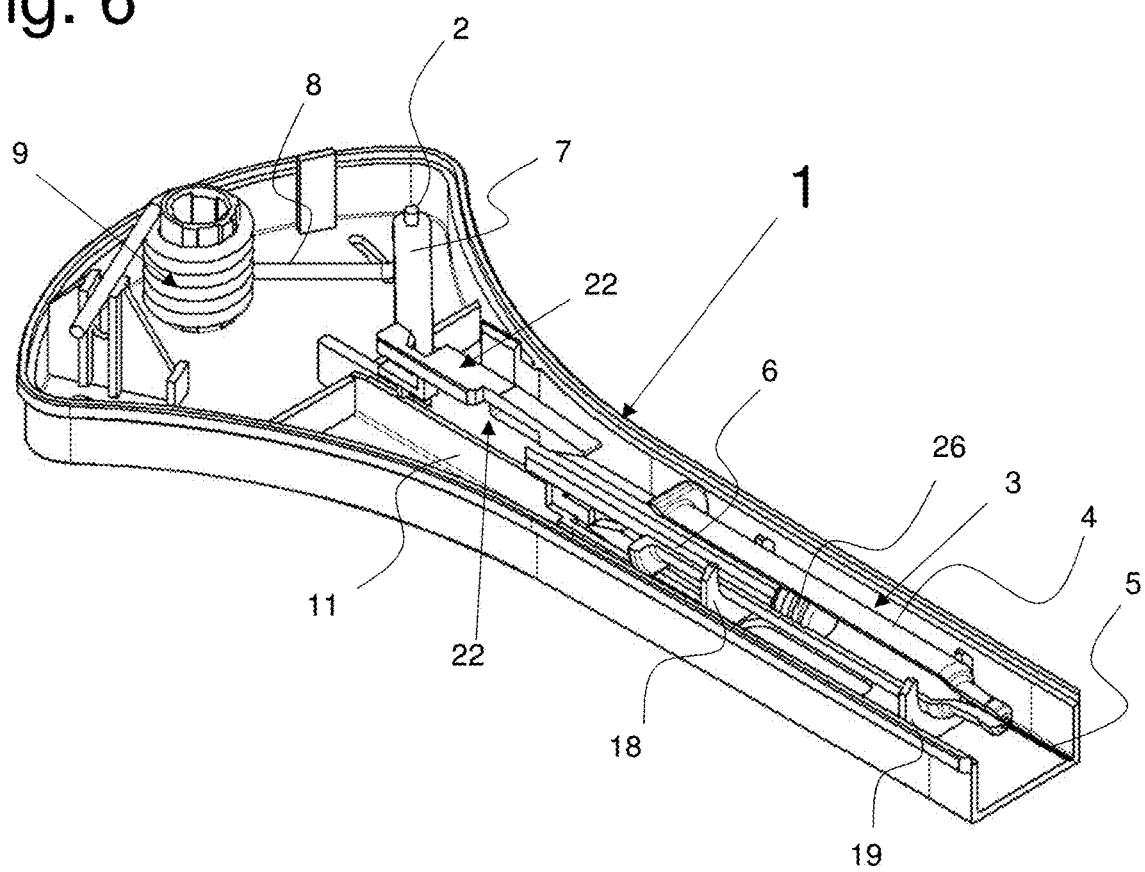
FIG. 6: This self-injector during injection, after the plunger has traveled about half of its path.
Figure 7:
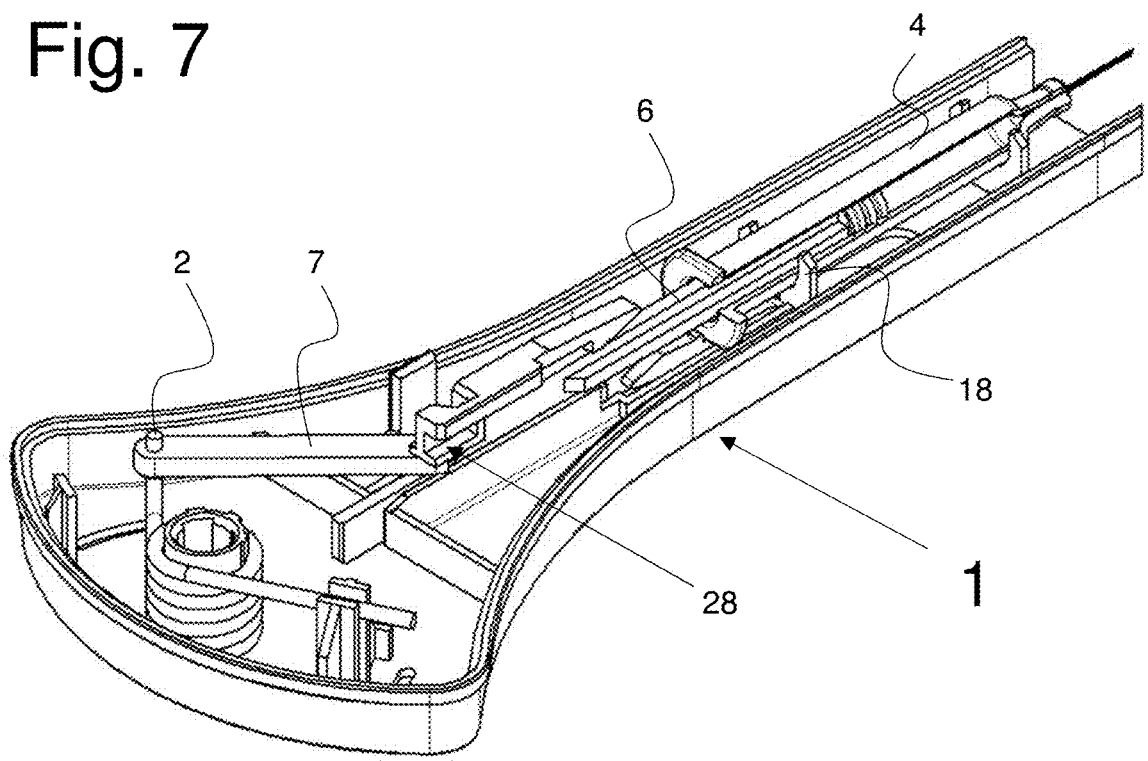
FIG. 7: This self-injector according to FIG. 6 seen from the rear side.

In FIG. 6, the self-injector is shown in the further course of the injection after the piston 6 has traveled approximately half of its path. The sealing pin 26 is now approximately in the middle of the cylinder 4 of the syringe 3. The movable spring leg 8 continues to pivot, as does the pivot lever 7 attached to it. As can be seen, the spring leg 8 forms a knee joint 2 together with the pivot lever 7. The force introduced into the pivot lever 7 by the spring leg 8 naturally decreases as the pivoting movement of the spring leg 8 progresses. At the same time, the more elongated this knee joint 2 is, the more impact force can be applied to the piston slide 22. This is important because it ensures that the ejection force acting on the sealing pin 26 remains uniform throughout the injection process. FIG. 7 shows the self-injector in the position shown in FIG. 6, viewed from the other, rear side.

Figure 8:
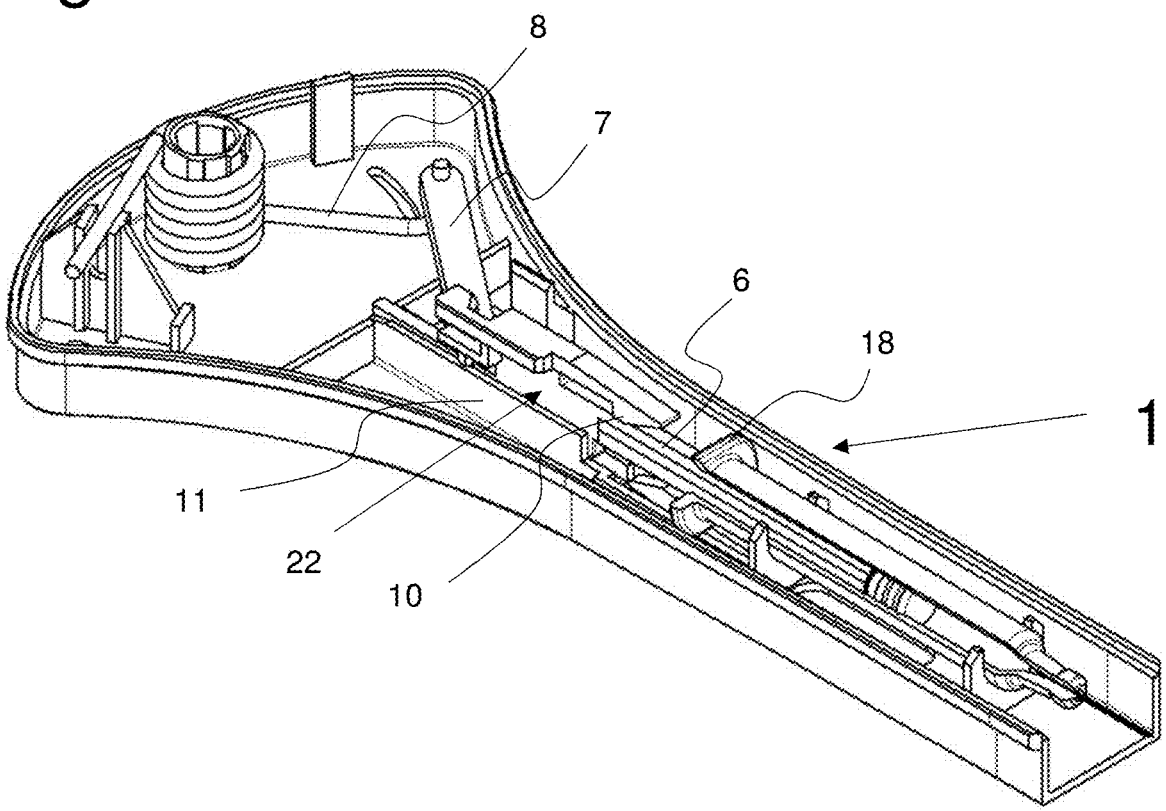
FIG. 8: This self-injector during injection, after the plunger has traveled about two thirds of its path for ejecting the active substance.
Figure 9:
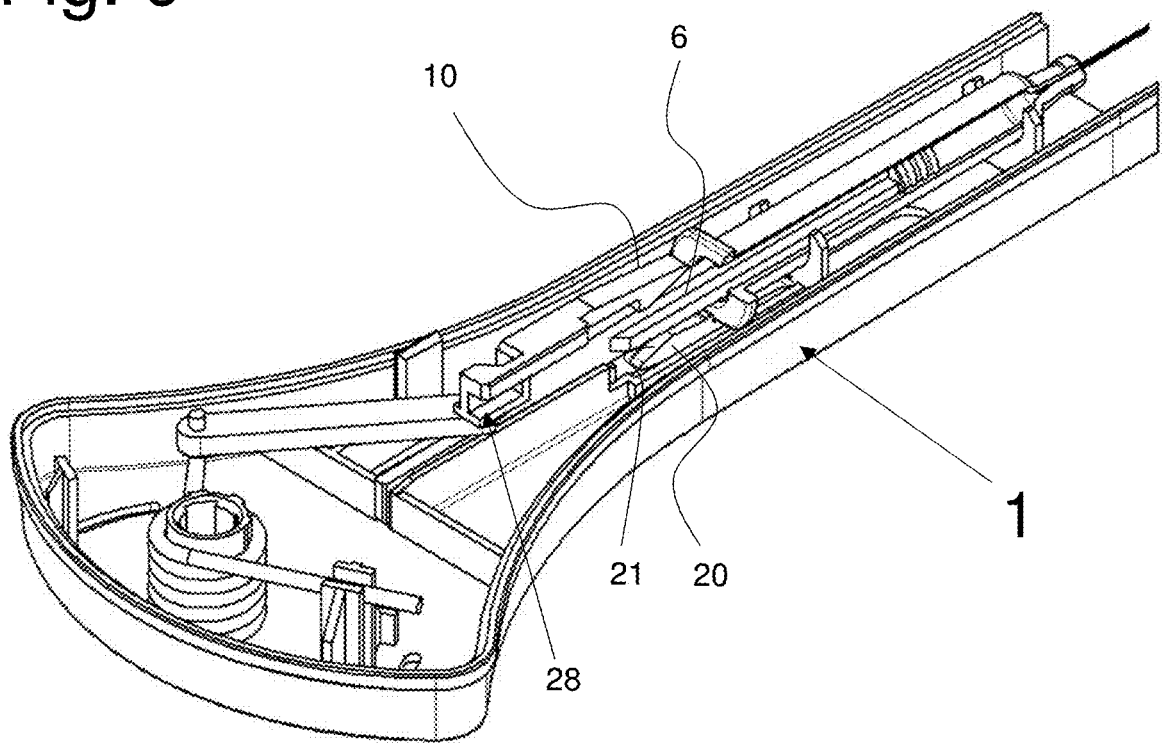
FIG. 9: This self-injector according to FIG. 8 as seen from the rear.

FIG. 8 shows the self-injector during injection, after the piston 6 has traveled about two thirds of its path for ejecting the active substance. Accordingly, the movable spring leg 8 has swiveled further and has also swiveled the swivel lever 7 hinged to it further, so that its front end pushed the plunger slide 22 further forward along the rail 11. The FIG. 9 shows the self-injector in the position shown in FIG. 8, viewed from the other, rear side.

Figure 10:
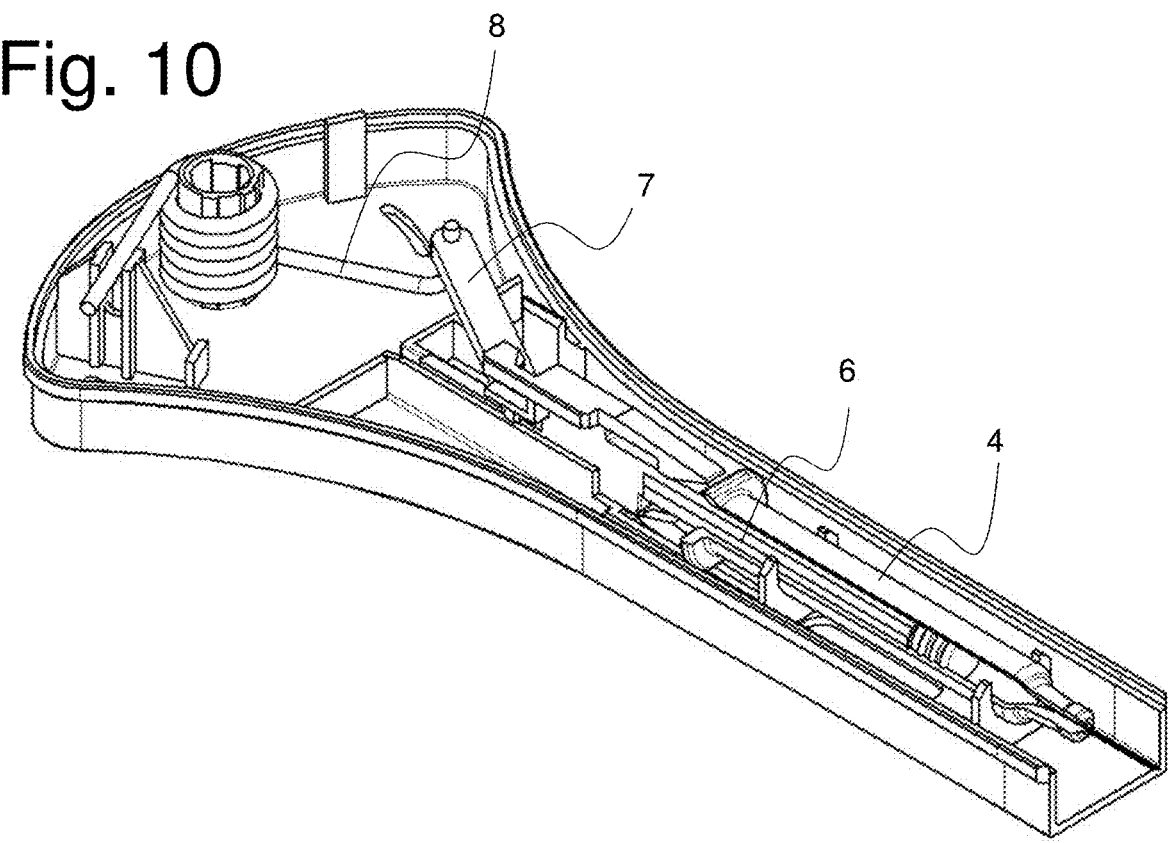
FIG. 10: This self-injector during injection, after the plunger has traveled almost its entire path for ejecting the active ingredient.
Figure 11:
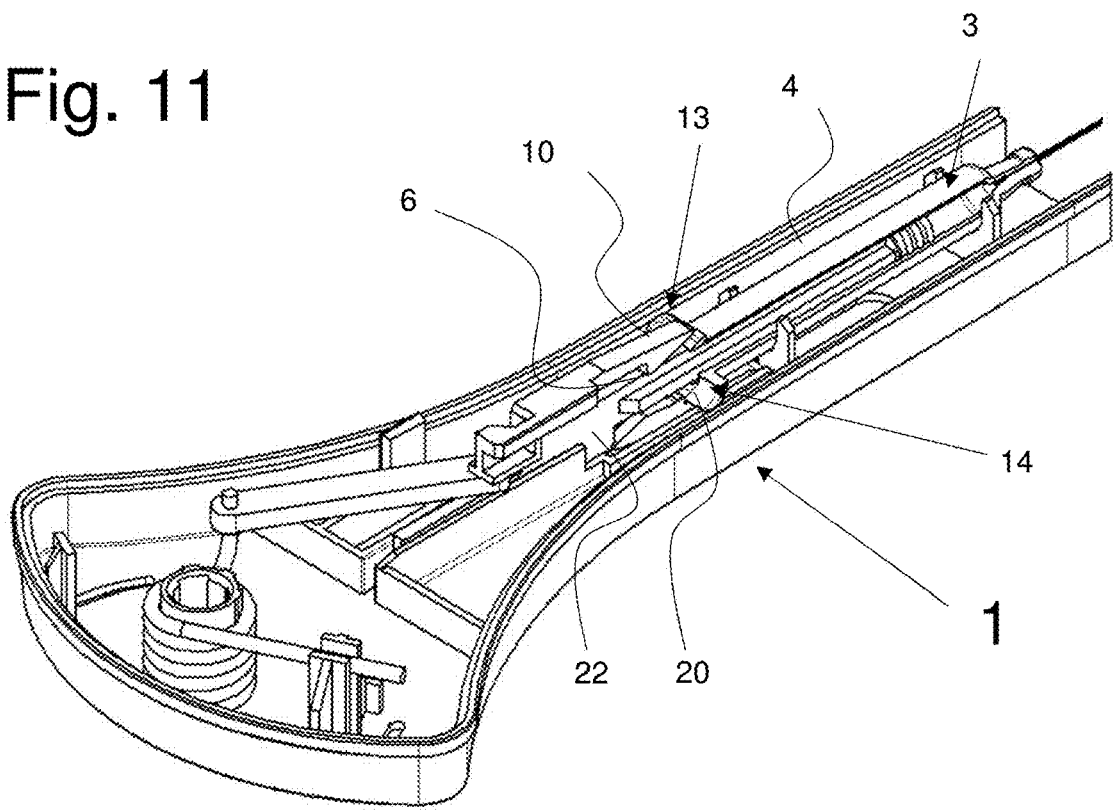
FIG. 11: This self-injector according to FIG. 10 seen from the rear side.

In FIG. 10, the self-injector is shown during injection after the plunger 6 in the barrel 4 has traveled almost its entire distance for ejecting the active ingredient, and in FIG. 11, this position is shown as seen from the other, rear side of the self-injector. The barb 10 on the plunger slide 22 is in relation to the rear end of the syringe 3 shortly before it is driven onto the flange 14 at the rear end 13 of the syringe 3 in order to engage with this flange 14.

Figure 12:
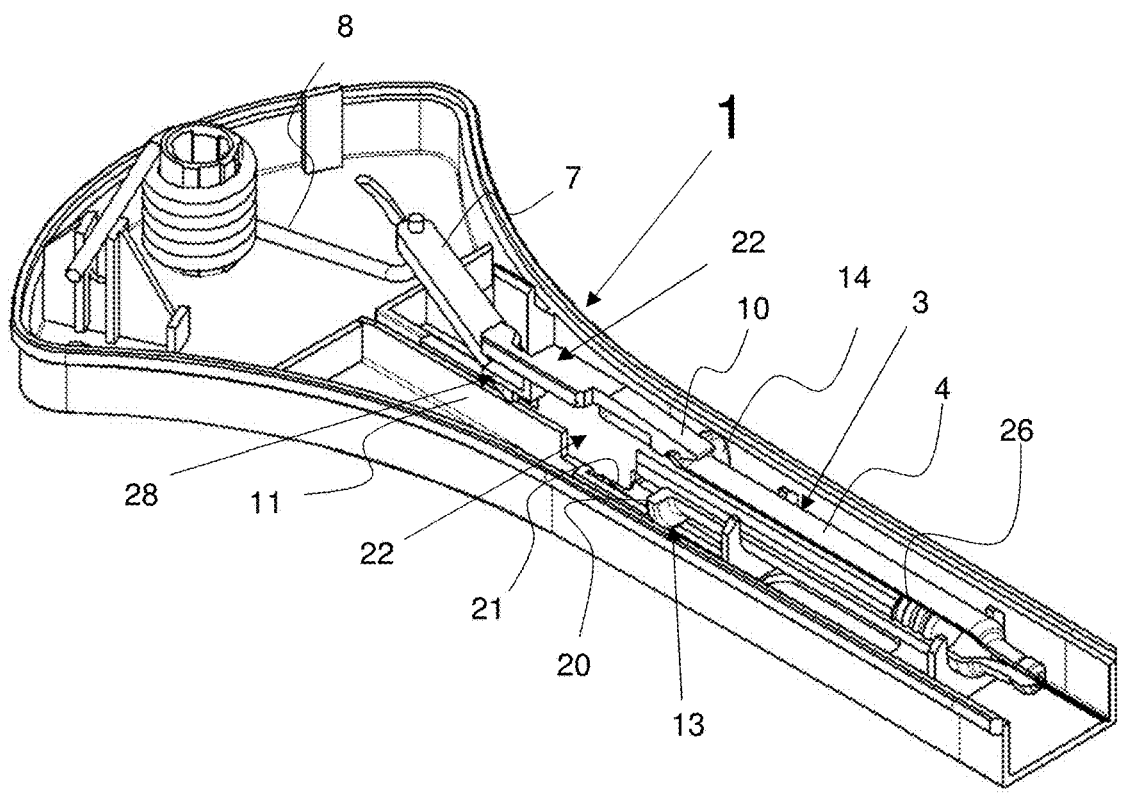
FIG. 12: This self-injector in the final phase of the forward movement of the plunger.
Figure 13:
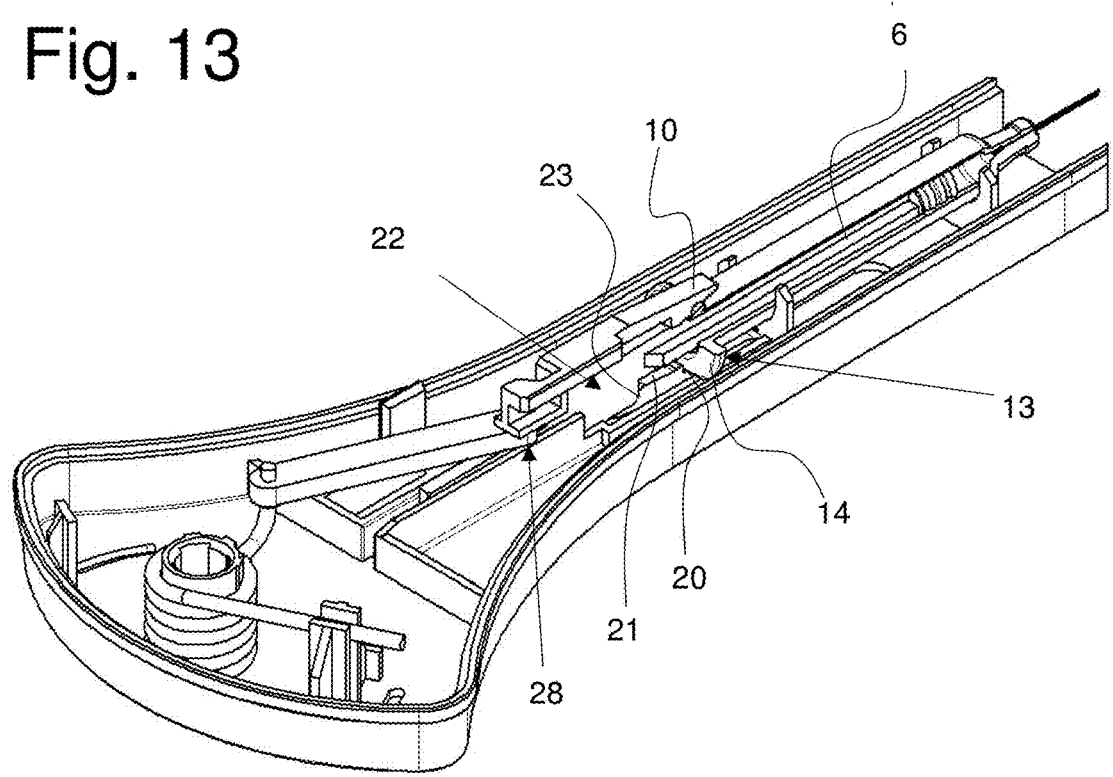
FIG. 13: This self-injector according to FIG. 12 seen from the rear side.

FIG. 12 shows the self-injector in the final phase of the piston movement. The sealing pin 26 in the syringe 3 or in its cylinder 4 has almost reached the front end. And the swivel lever 7 for pushing the plunger slide 22 forward is only slightly angled away from the direction of the rail 11. As you can see, the barb 10 is already halfway onto the flange 14 at the rear end of the syringe 3. At the same time, the piston slide 22 has already moved a little way up the inclined ramp 21 in order to push the elastic leg 29 downwards, whereby the stop 20 releases the flange 14 so that the syringe 3 can be pulled backwards unhindered by the barb 10. FIG. 13 shows the same situation as seen from the other, rear side of the self-injector.

Figure 14:
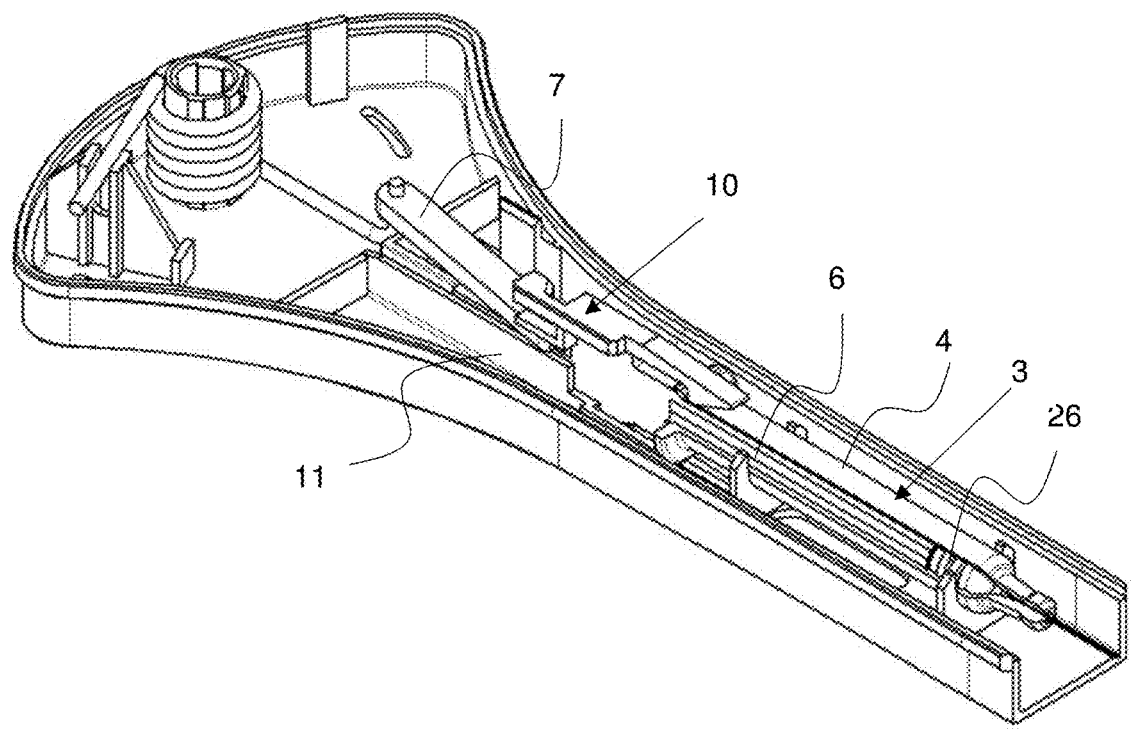
FIG. 14: This self-injector at the end of the forward movement of the plunger, with the barb attached for withdrawing the syringe in a subsequent injection phase.
Figure 15:
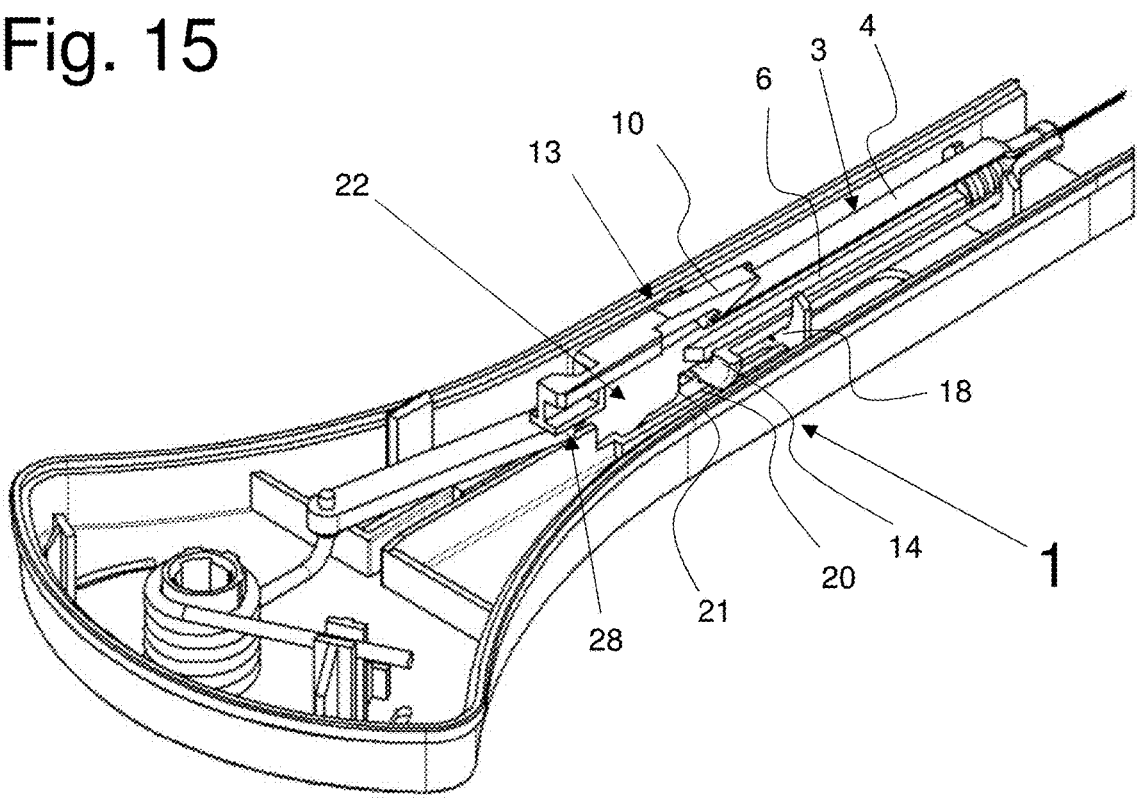
FIG. 15: This self-injector according to FIG. 14 seen from the rear side.

FIG. 14 shows the self-injector shortly before the end of the piston movement. The swivel lever 7 is now almost exactly aligned with the rail 11 and the piston 6 is pushed into the cylinder 4 of the syringe 3 almost as far forward as possible. The further FIG. 15 shows the same from the other, rear side of the self-injector, with the barb 10 driven onto the flange 14 at the end 13 of the syringe 3 after being hooked onto this flange 14. For this purpose, the barb 10 is slightly elastically pushed upwards relative to the piston slide 22 and then falls down again like a latch behind the flange 14 due to the elastic restoring force and engages on the flange 14. The piston slide 22 has moved up onto the ascending ramp 21 and has pressed the elastic leg 29 and thus the stop 20 downwards, so that the syringe 3 can then be pulled back into the housing 1 unhindered.

Figure 16:
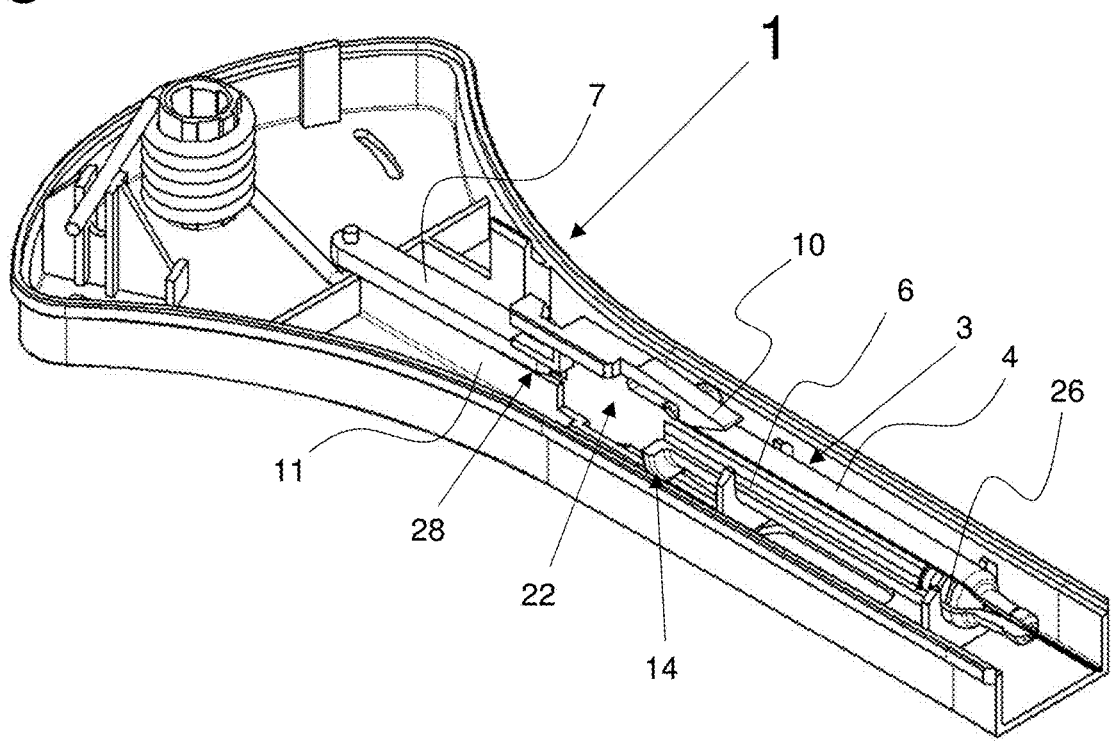
FIG. 16: This self-injector at the end of the injection.
Figure 17:
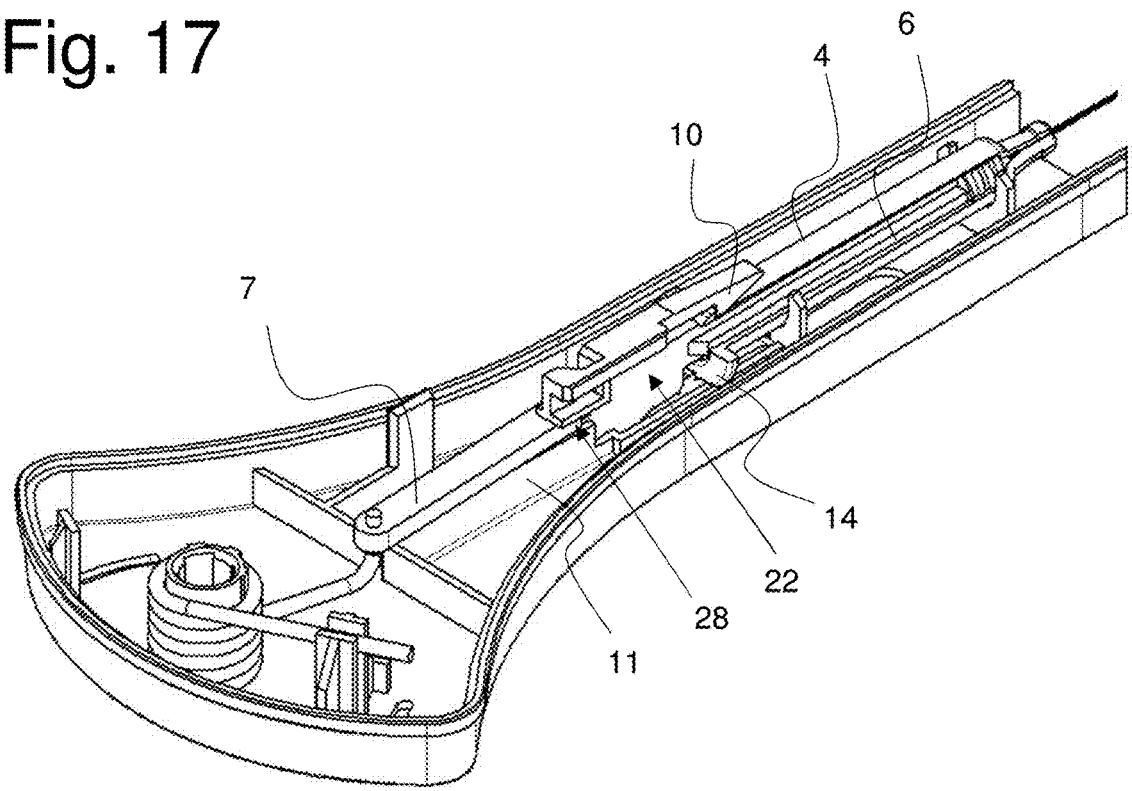
FIG. 17: This self-injector according to FIG. 16 seen from the rear side.

In the illustration according to FIG. 16, the self-injector is shown after completion of the injection phase. The barb 10 is now attached to the flange 14 of the syringe 3. The piston 6 has reached the front end of the cylinder 4 with the sealing pin 26. The swivel lever 7 is now approximately in the same straight line as the guide rail 11 for the plunger slide 22 and the plunger 6. Because the barb 10 is engaged on the flange 14, the syringe 3 is now ready to be retracted by the plunger slide 22 and the barb 10 in the subsequent phase. FIG. 17 shows this position as seen from the other, rear side of the self-injector.

Figure 18:
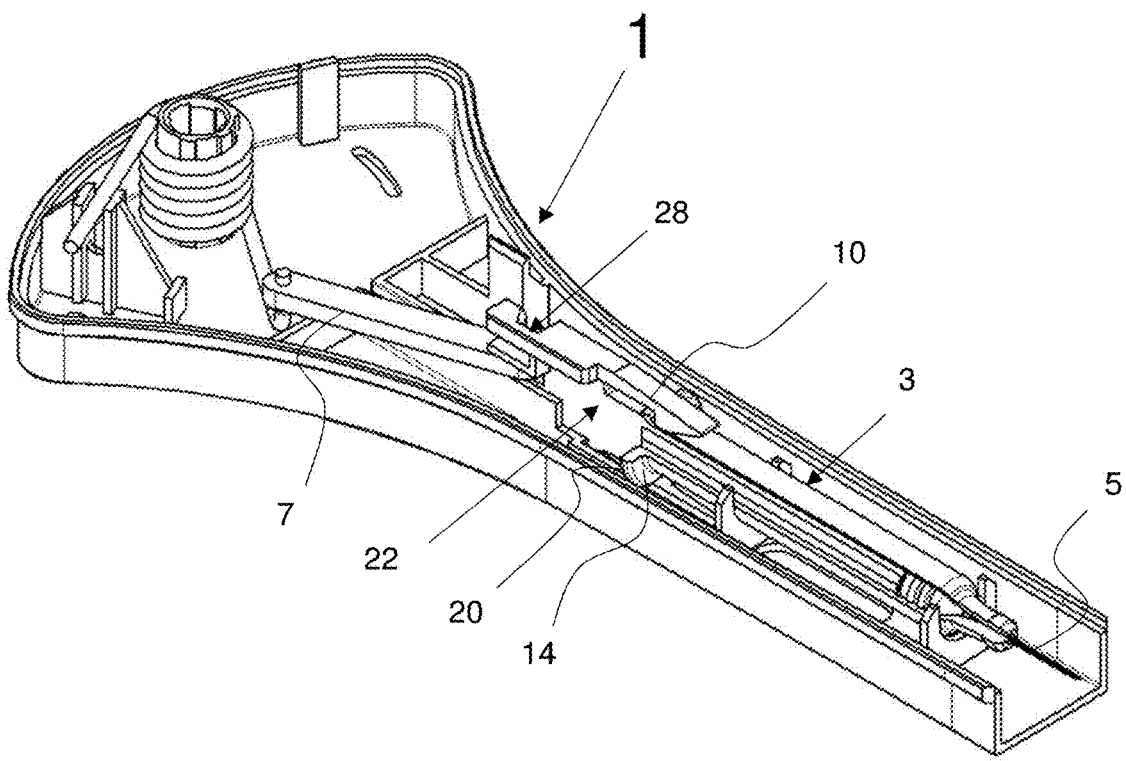
FIG. 18: This self-injector in the initial phase of withdrawing the syringe.
Figure 19:
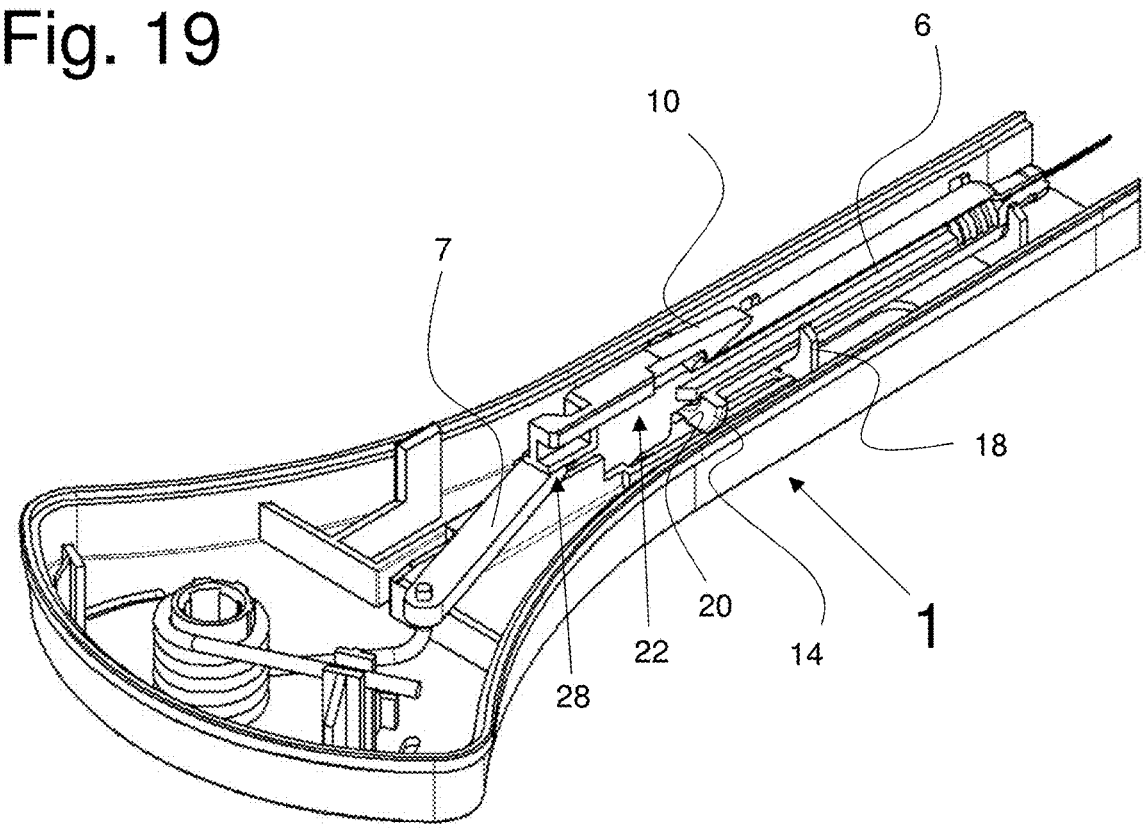
FIG. 19: This self-injector according to FIG. 18 seen from the rear side.

FIG. 18 shows the initial phase of retracting the syringe 3. Here, the swivel lever 7 has already swiveled further beyond the direction of the rail 11 and pulls it into the housing 1 with its front articulation 28 on the plunger slide 22. The barb 10 on the plunger slide 22 therefore pulls the syringe 3 back at its rear flange 14 and thus also the needle 5 into the housing 1. FIG. 19 shows the same position of the swivel lever 7 as seen from the other, rear side of the self-injector. Here, too, you can see how the syringe 3 with its flange 14 can be retracted unhindered past the downwardly pressed elastic leg 29 and stop 20 by the barb 10 and the piston slide 22.

Figure 20:
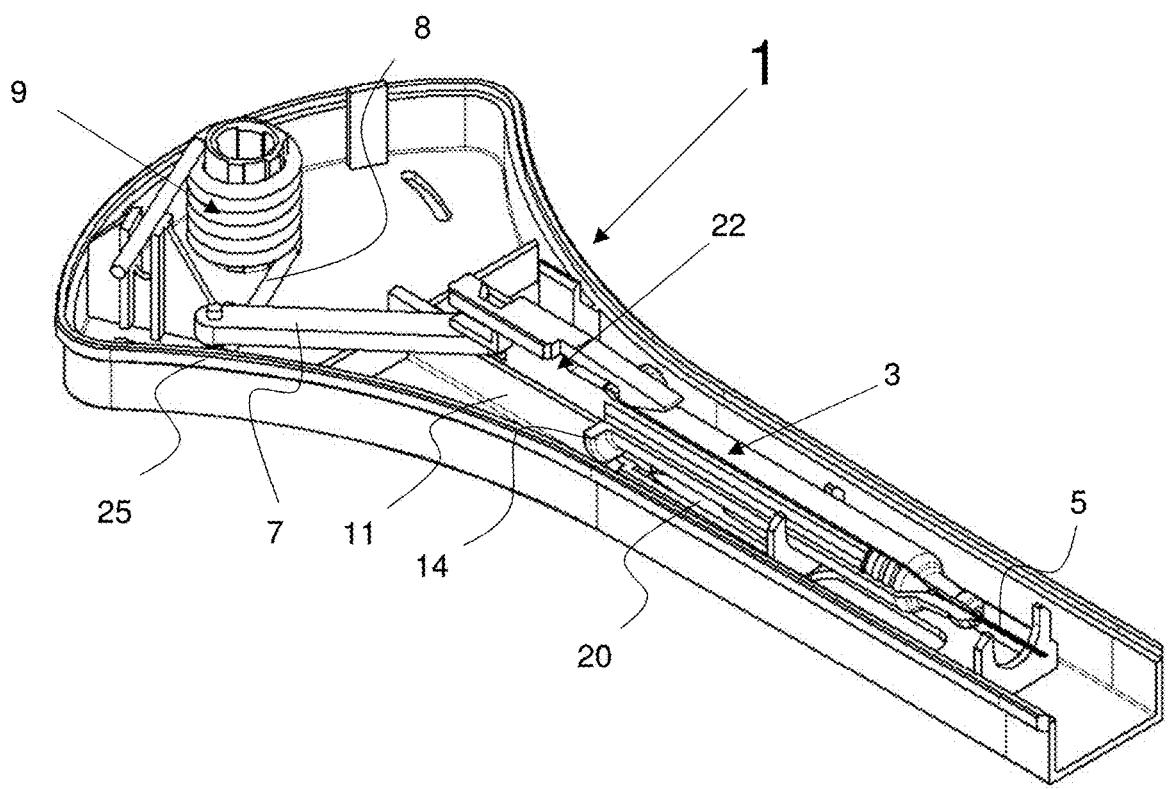
FIG. 20: This self-injector after the syringe and its needle have been fully withdrawn into the interior of the housing.
Figure 21:
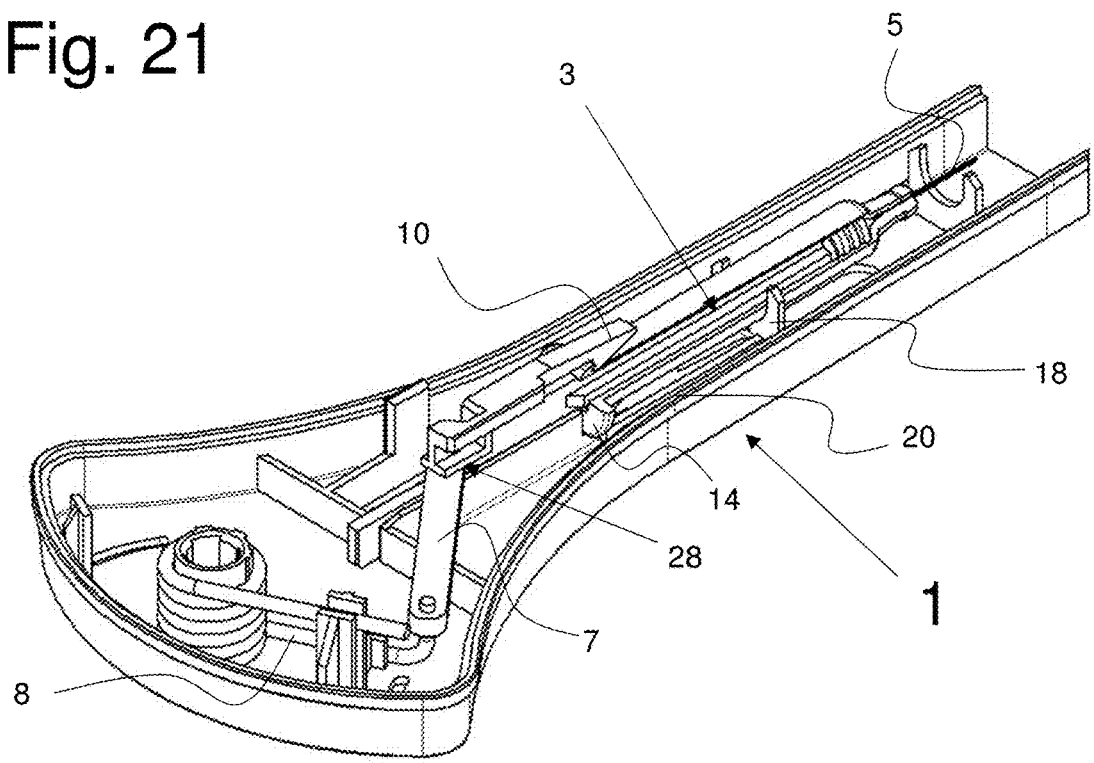
FIG. 21: This self-injector according to FIG. 20 seen from the rear side.

At the end of the entire action of the swivel lever 7 by means of the torsion spring 9, the situation is as shown in FIG. 20. The movable spring leg 8 has reached its stop 25 in the housing 1 and has swiveled the swivel lever 7 to this point. Because the front end of the swivel lever 7 is hinged to the piston slider 22, the swivel lever 7 has retracted the piston slider 22 and with it the entire syringe 3 via the barb 10, so that its needle 5 has finally been pulled completely into the housing 1 and can no longer injure or infect anyone. Finally, FIG. 21 shows this situation as seen from the other, rear side of the self-injector. The syringe 3 has been pulled backwards past the stop 20 by the barb 10 on the flange 14. The needle 5 of the syringe 3 has disappeared into the housing 1.

Figure 22:
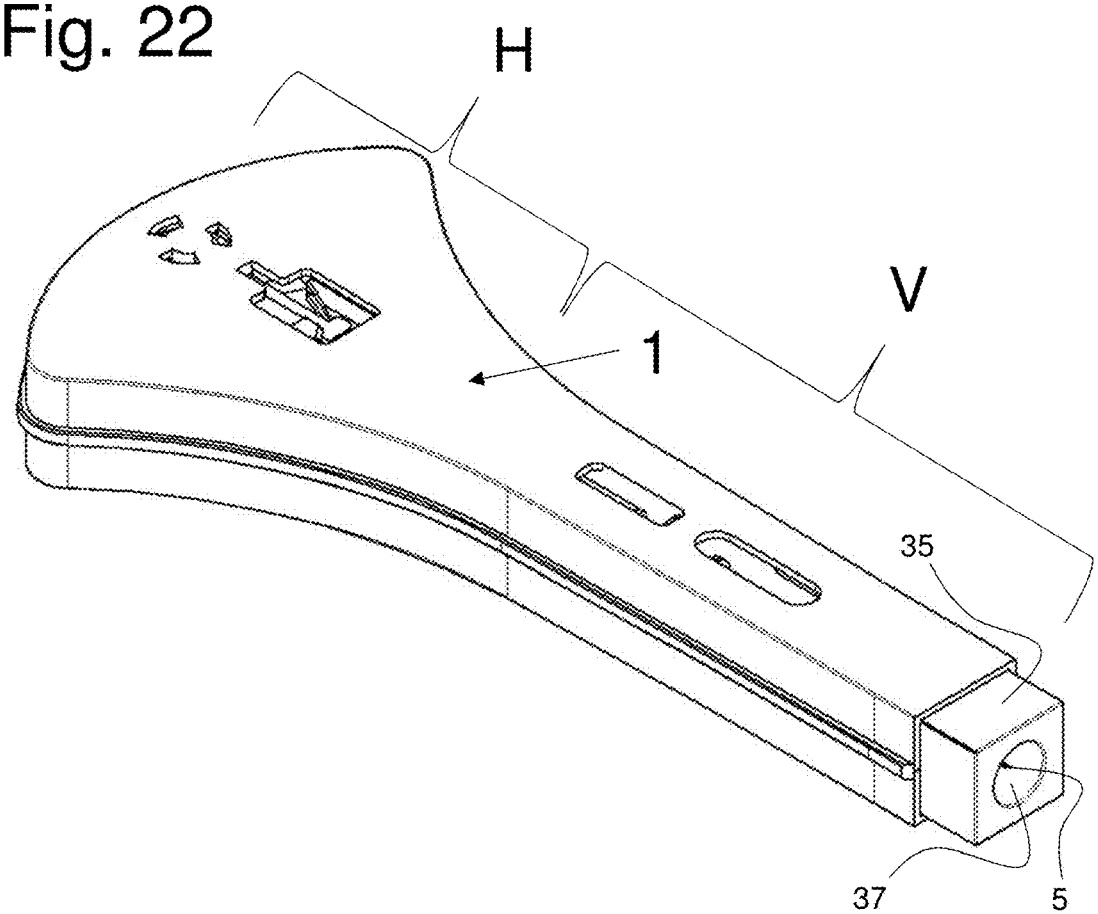
FIG. 22: The self-injector with the housing closed.

It is understood that the lower housing part shown in these FIGS. 1 to 21 has a congruent upper housing part which can be clicked onto the lower housing part, forming a closed housing 1, so that the self-injector then appears as shown in FIG. 22.

In its front part V, into which the syringe 3 is inserted, the housing 1 of this self-injector forms a channel which is rectangular in cross-section and in which the piston slide 22 is also guided with its upper side, i.e. also on the inside of the upper housing part. The rear part H of the housing 1 widens out from this rectangular channel towards the rear on both sides in a fan shape. The needle 5, the torsion spring 9 and the tube 47 on the extractor 46 (FIG. 1) are the only metal parts on a self-injector loaded with a syringe. All other parts of this self-injector can be made of injection-molded plastic and, if necessary, the puller can also be made of plastic. Assembly is simple, as there are only a few parts to assemble, namely only seven parts in addition to the syringe 3 consisting of cylinder 4, sealing plug 26, enclosed active ingredient and needle 5 with protective cap 27, namely:

1. Lower housing section
2. Upper housing section
3. Torsion spring 9
4. Swivel lever 8
5. Piston slide 22 with integral molded piston 6 and barb 10
16. Release slide 30 for release, with release displacer 45 (from FIG. 23)
7. Puller 46 with tube 47 and barb 48 therein, as shown in FIG. 1. The release slide 30 with its release displacer 45 and its function are described in more detail with reference to FIGS. 23-34.

Figure 35:
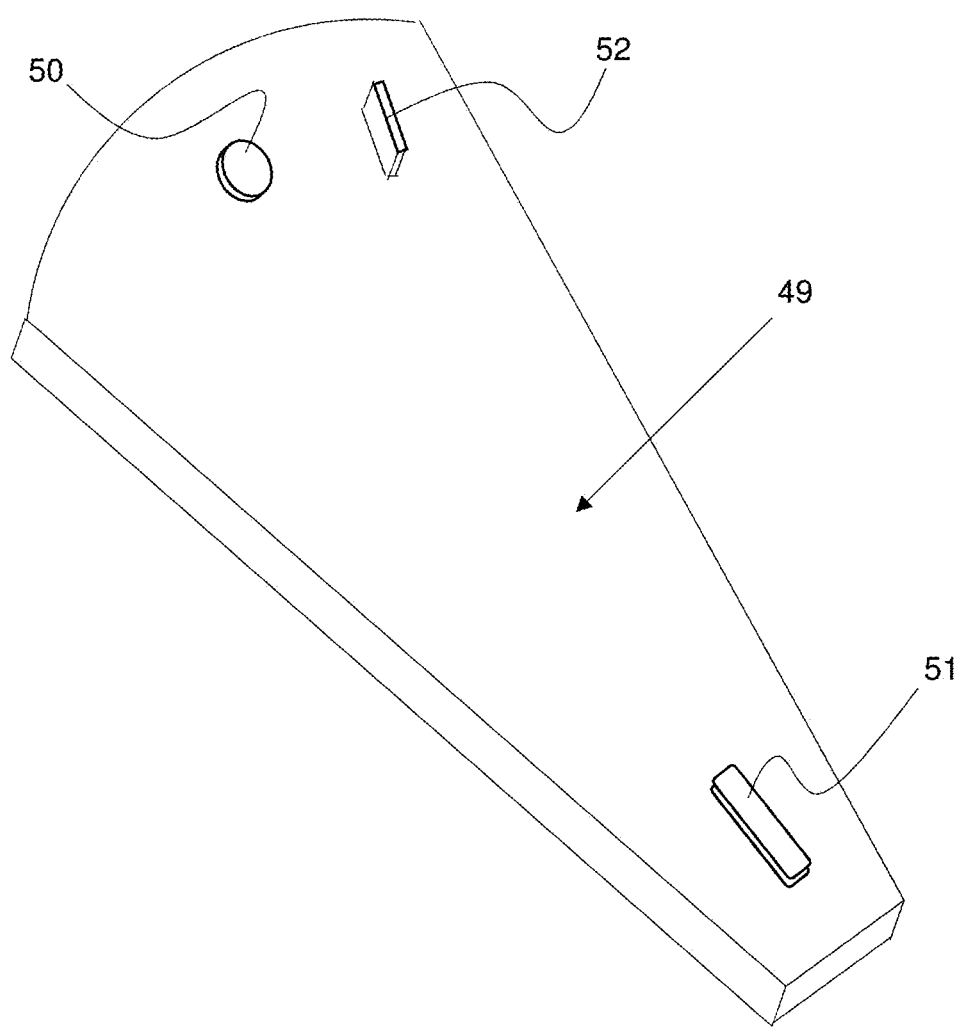
FIG. 35: A securing plate for placing the self-injector on top for assembly.

Assembly is carried out as follows. The lower housing part is positioned on an assembly aid 49, as shown in FIG. 35. The torsion spring 9 is inserted over the bolt 16 in the housing 1 in such a way that the spring leg 17 is mounted stationary and strikes and is held against the housing 1 in a correspondingly shaped retainer 24, and that the spring leg 8 is pretensioned with the application of force into its initial position and is there temporarily blocked in its position, for example by means of a cam 52 on the mounting plate 49. The pivot lever 7 is clipped into the joint 28 at the rear end of the piston slide 22. The pre-assembled parts of the swivel lever 7 and piston slide 22 are now inserted into the rail 11 in the lower housing section. At the same time, the rear end of the swivel lever 7 is connected to the end of the movable spring leg 8 via the linkage point 2. The puller 46 with its tube 47 with its barbs 48 is placed on the protective chamber 35 of the release slide 30. The syringe 3 consisting of cylinder 4, sealing pin 26, enclosed active ingredient and needle 5 with protective cap 27 is now pushed through from the rear end of the trigger slide 30 with the puller 46 attached, so that the protective cap 27 passes through the hole 37 of the protective chamber 35 and engages with the barbs 48. The pre-assembled parts trigger slide 30, syringe 3 and extractor 46 are inserted into the lower part of the housing so that the piston 6 at the front end of the piston slide 22 is inserted into the open end of the cylinder 4 of the syringe 3 without touching the sealing pin 26. The upper housing part is now placed onto the lower housing part. The release pawl 33 of the upper housing part plunges into the recess 32 in the piston slide 22. The assembled housing can now be removed from the mounting plate 49. This causes the cam 52 to release the preloaded spring leg 8. However, the piston slide 22 is released by the release pawl 33 is initially held back by a release slide 30 so that the spring leg 8 remains tensioned. This release pawl and the release of the self-injector are described in detail in the following figures.

Figure 23:
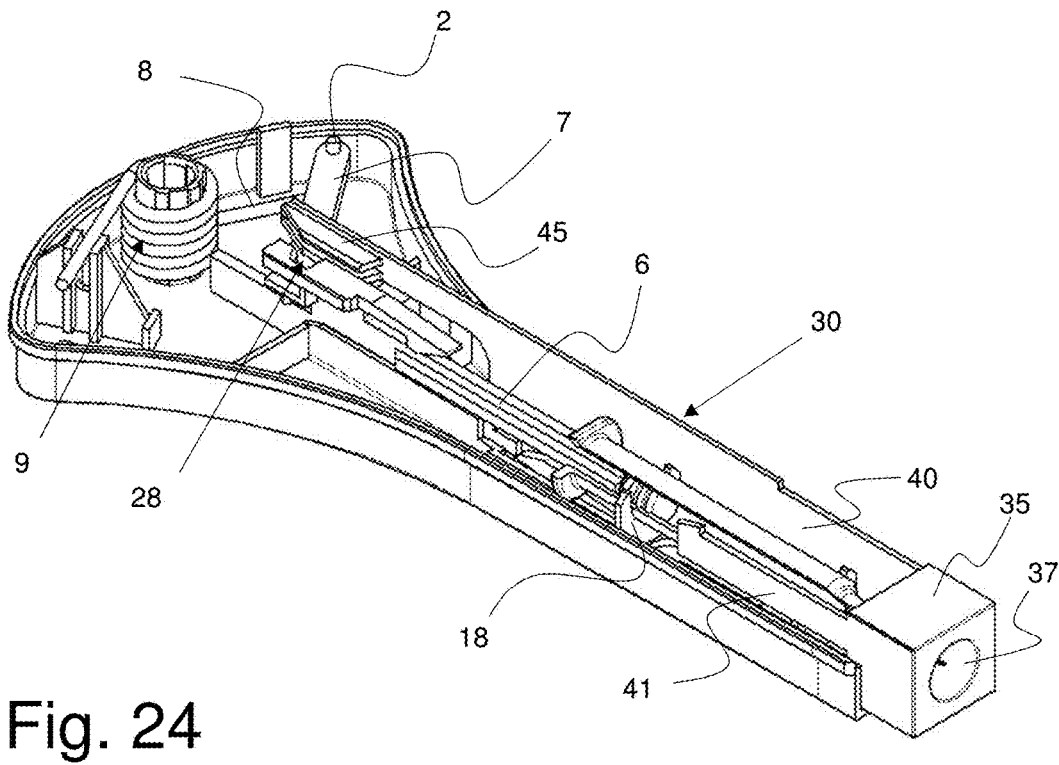
FIG. 23: The self-injector shown in FIG. 22 with the housing open at the top, in the cocked initial state.

FIGS. 22 to 32 show the self-injector with the release slide 30 now inserted. Initially, this self-injector was shown in FIG. 22 with the housing closed. In FIG. 23, the upper part of the housing has been removed again and, as can be seen, the self-injector is here in the tensioned initial position, i.e. with the torsion spring 9 tensioned. The movable spring leg 8 is held back in this tensioned state because the piston slide 22 is blocked and held back by a pawl. The release slide 30, which forms a displacer 45 at its rear end and is guided on the housing by a slide plate 40, is now inserted here for the first time. On the opposite side of the slide plate 40, a second guide plate 41 is formed on the protective chamber 35, which can also be moved along the housing.

Figure 24:
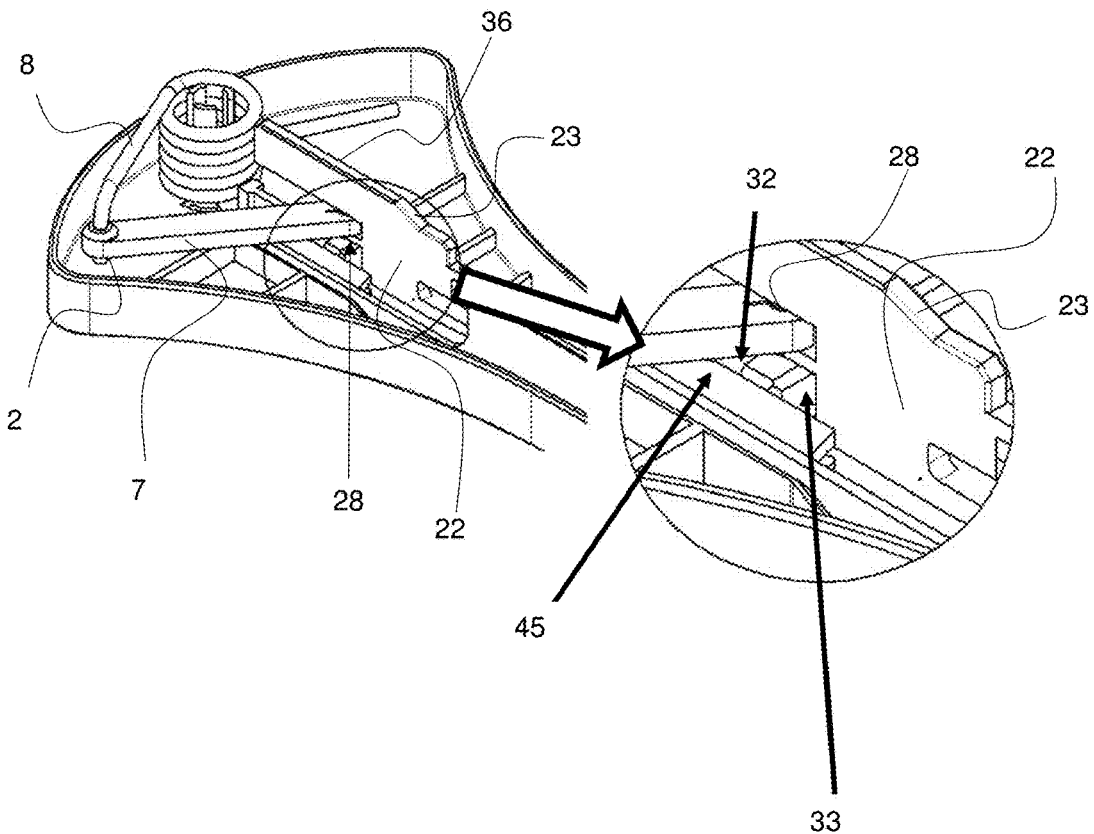
FIG. 24: A detail of the locking mechanism of the self-injector, here in a position rotated by 180° around the longitudinal axis compared to FIG. 23, with a view into the interior of the upper part of the housing, and on the right below the circular cut-out in an enlarged view.

FIG. 24 shows a detail of the locking mechanism of the self-injector. The illustration shows the construction in a position rotated by 180° about the longitudinal axis of the housing 1 with respect to the illustration in FIG. 23, without the lower housing part shown so far, but with the upper housing part with a view into its interior, and on the right below the circular cut-out in an enlarged view. Here you can see the piston slide 22, the lower edge 36 of which is at the top in this figure, an inclined surface or ramp 23, with which the piston slide 22 can move onto the ramp 21 in order to push away the elastic leg 29 and thus the stop 20, so that the syringe 3 can then be withdrawn unhindered into the housing 1

The enlarged view of the locking mechanism shows the pawl 33, which can be swung out laterally in the housing, and the displacer 45, which now rests laterally against it and holds the pawl 33 in a recess 32 in the piston slide 22, so that the piston slide 22 cannot move in the direction of syringe 3.

The sequence of movements from the triggering of this self-injector can be seen from the following description.

Figure 25:
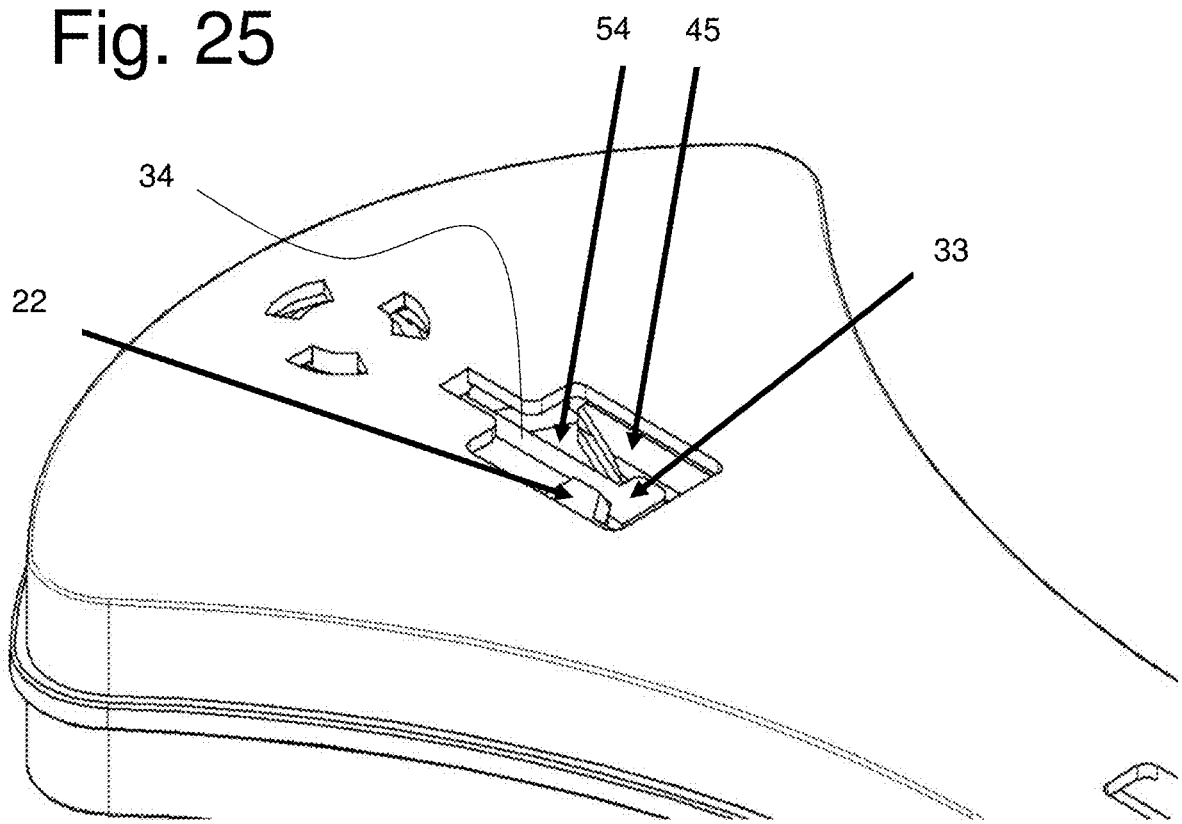
FIG. 25: an enlarged section of the top of the housing in FIG. 22, with the windows cut out to reveal the interior.

FIG. 25 shows the rear part of the upper part of the housing with a window 44, which provides a view into the interior. In this window 44, a latch 33 can be seen at the end of an elastically pivotable arm 34, which is formed on the housing part. This latch 33 can pivot elastically back and forth at right angles to this arm. The displacer 45 of the release slide 30 is in contact with the outer edge of the pawl 33 at the rear in the picture and thus presses the pawl 33 against its elastic restoring force into the recess 32 in the piston slide 22. The piston slide 22 is thus blocked and cannot be displaced in the direction of the syringe 3. The spring leg 8 and the swivel arm 7 are also prevented from swiveling.

Figure 26:
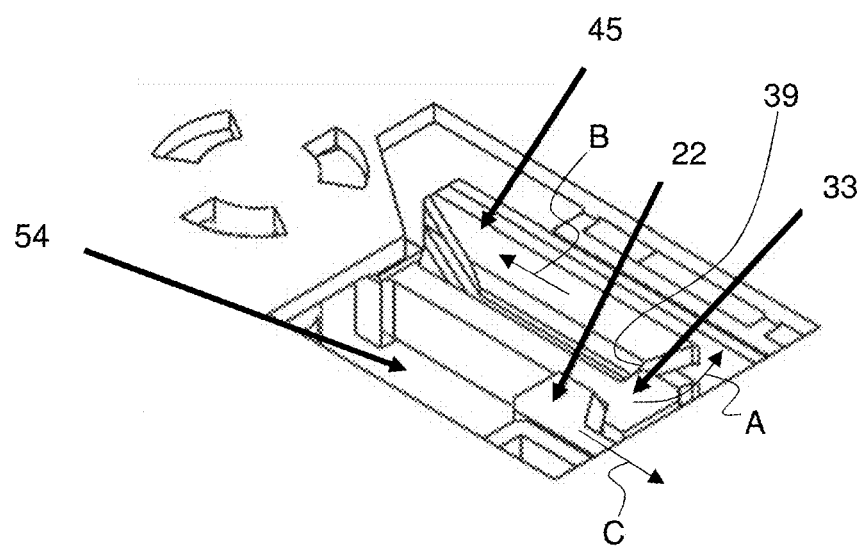
FIG. 26: A view of these windows as shown in FIG. 25, again enlarged to distinguish the parts visible inside.

In FIG. 26, a further enlarged representation of the window or the recess 44 in the upper part of the housing shows how the release slide 30 was pushed backwards into the housing by applying the self-injector, i.e. by pressing the protective chamber 35 onto the planned insertion point, according to arrow B. The displacer 45 was thus pushed past this latch 33 in a sliding manner. The displacer 45 was thus slid past the release slide 30 at this latch 33. This sliding past takes place until the rear edge 39 of the release mechanism 45 passes the latch 33 and releases it for pivoting towards the release slide 30. As a result, the arm 34 of the pawl 33 swivels out of the recess 32 on the plunger slide 22, as shown by arrow A, and releases it abruptly for displacement in the direction of the syringe 3. The piston slide 22, driven by the pretensioned spring leg 8 and the pivot lever 7 hinged to it, with which it forms a toggle lever, then pushes the piston 6 forward inside the syringe 3 according to arrow C and the active substance is injected through the needle into the tissue.

Figure 27:
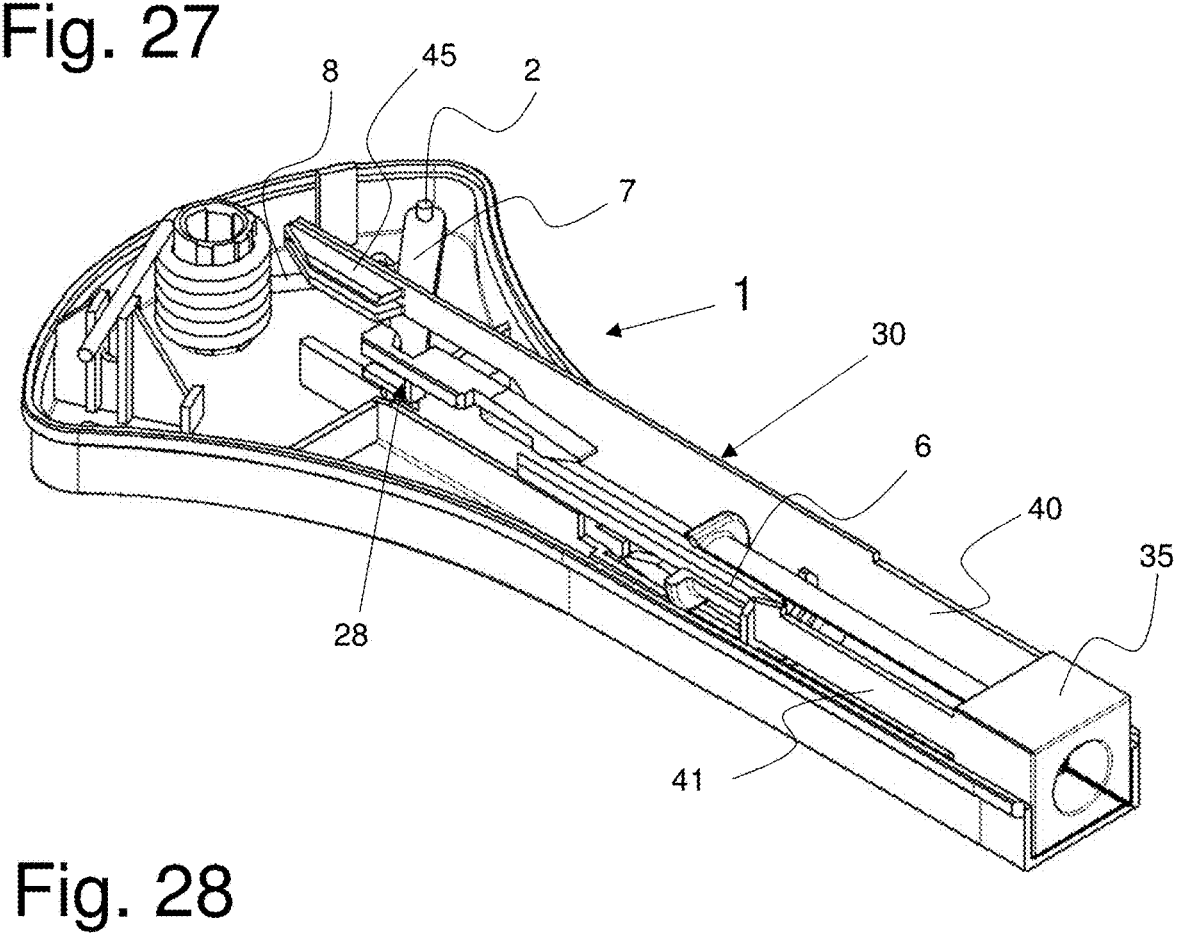
FIG. 27: The self-injector in its initial position, with the release slide with its displacer as a trigger for a latch.
Figure 28:
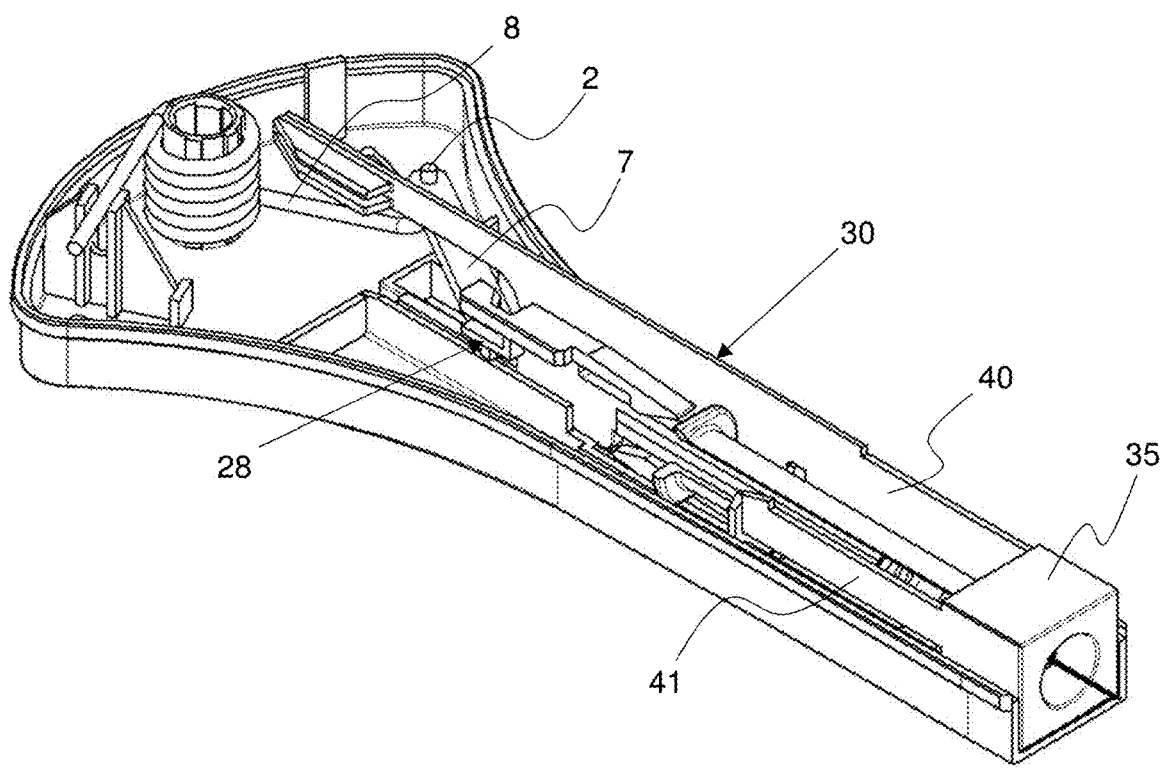
FIG. 28: The self-injector shown in FIG. 27 shortly after triggering.

FIG. 27 first shows the initial phase immediately after the release of the movable spring leg 8 after the pawl 33 has moved out of the way. It has already swiveled clockwise by a few degrees and accordingly took the articulated swivel lever 7 with it, which, however, as seen from the observer, is thus in the counterclockwise around the mobile pivot point 28. FIG. 28 shows the situation when the spring leg 8 has traveled a swivel path of approximately 30°.

Figure 29:
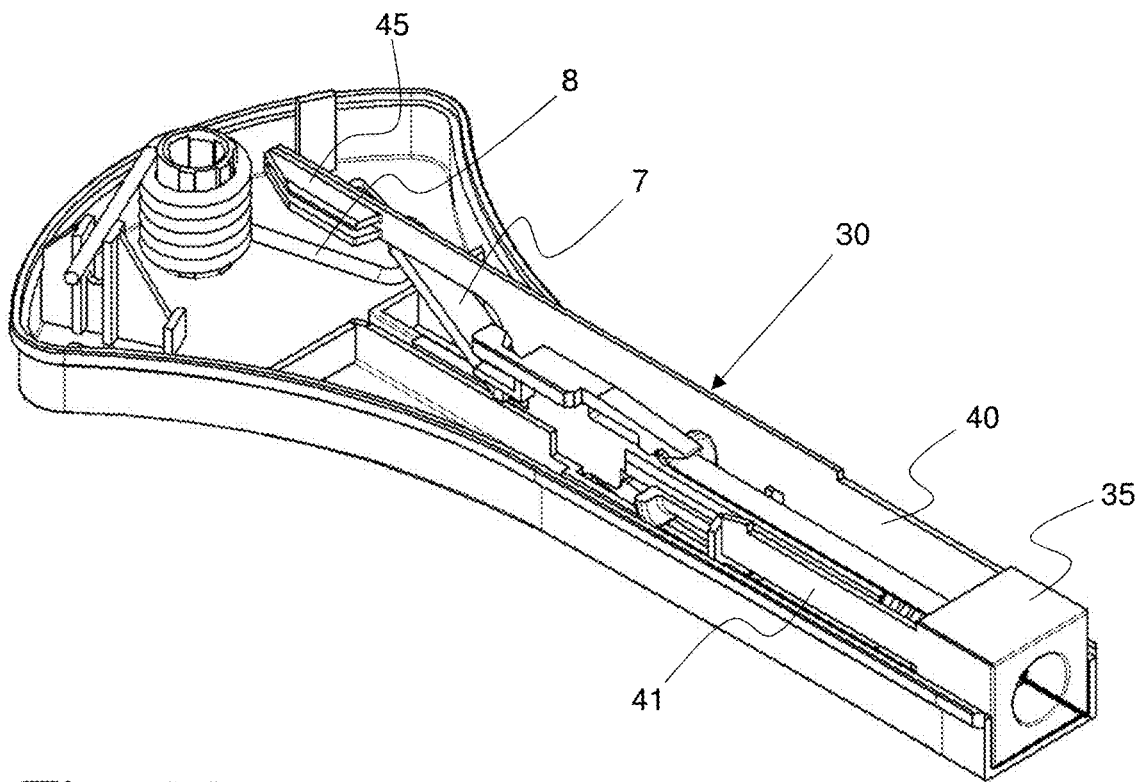
FIG. 29: The self-injector according to FIG. 27 after approximately half the travel of the spring leg.
Figure 30:
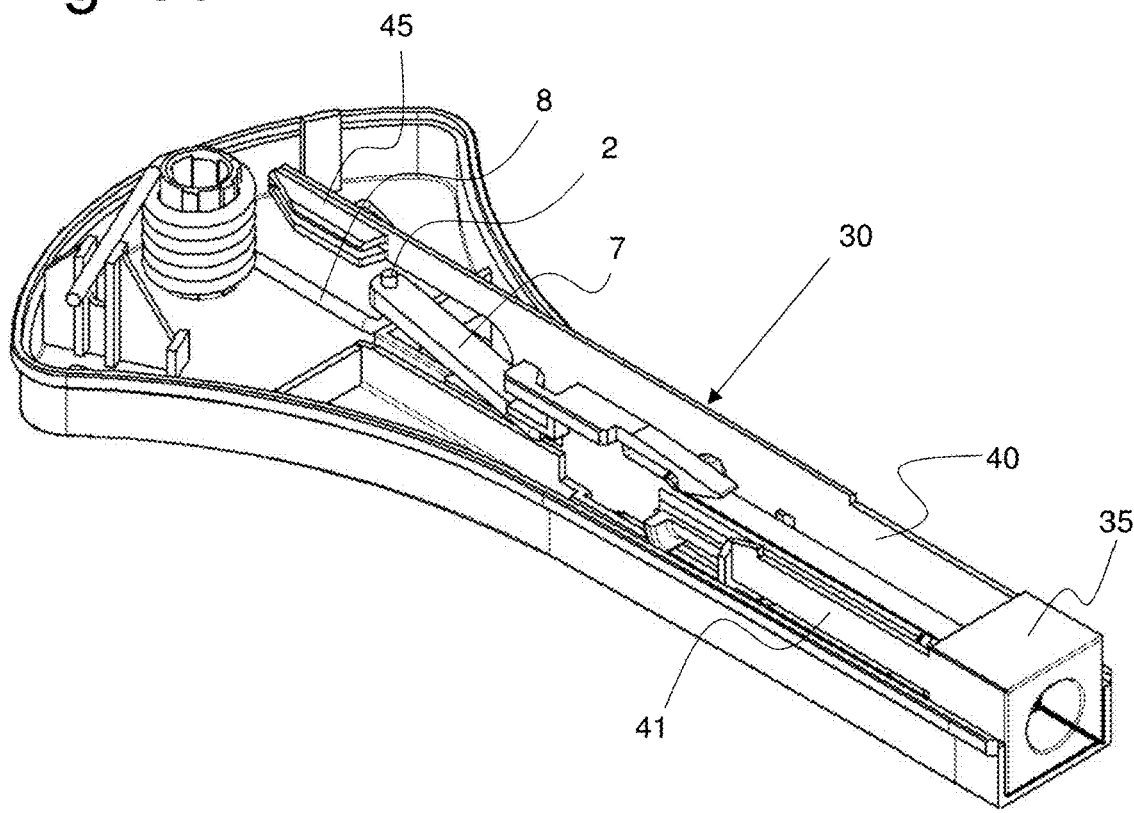
FIG. 30: The self-injector according to FIG. 27 at the beginning of the retraction of the syringe.
Figure 31:
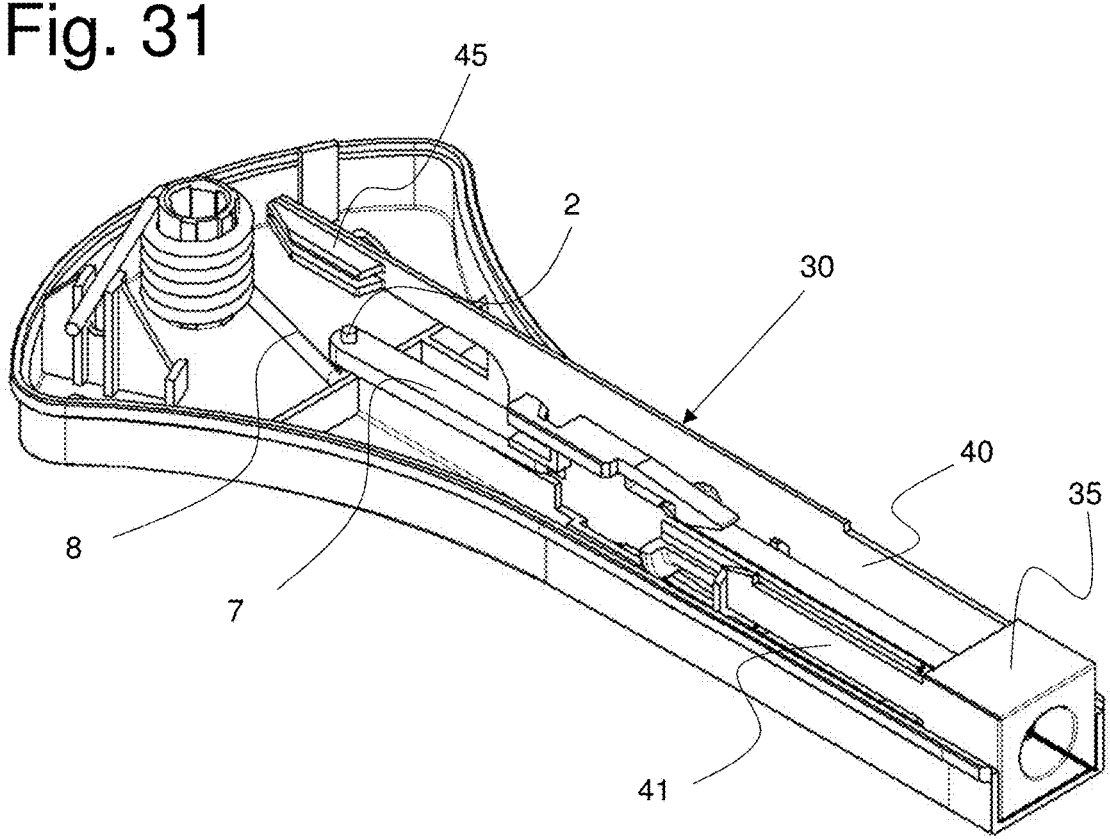
FIG. 31: The self-injector according to FIG. 27 after approximately ⅔ of the spring leg path has been covered.
Figure 32:
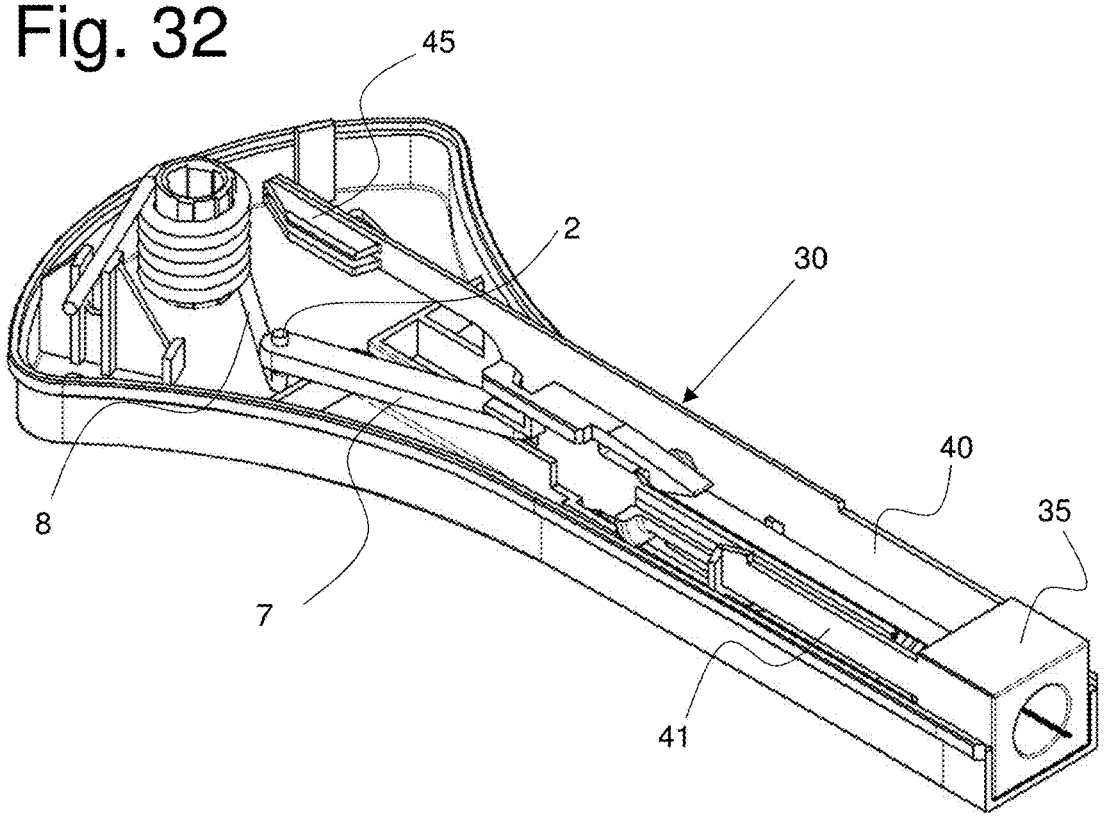
FIG. 32: The self-injector according to FIG. 27 after covering approx. ¾ of the spring leg path.
Figure 33:
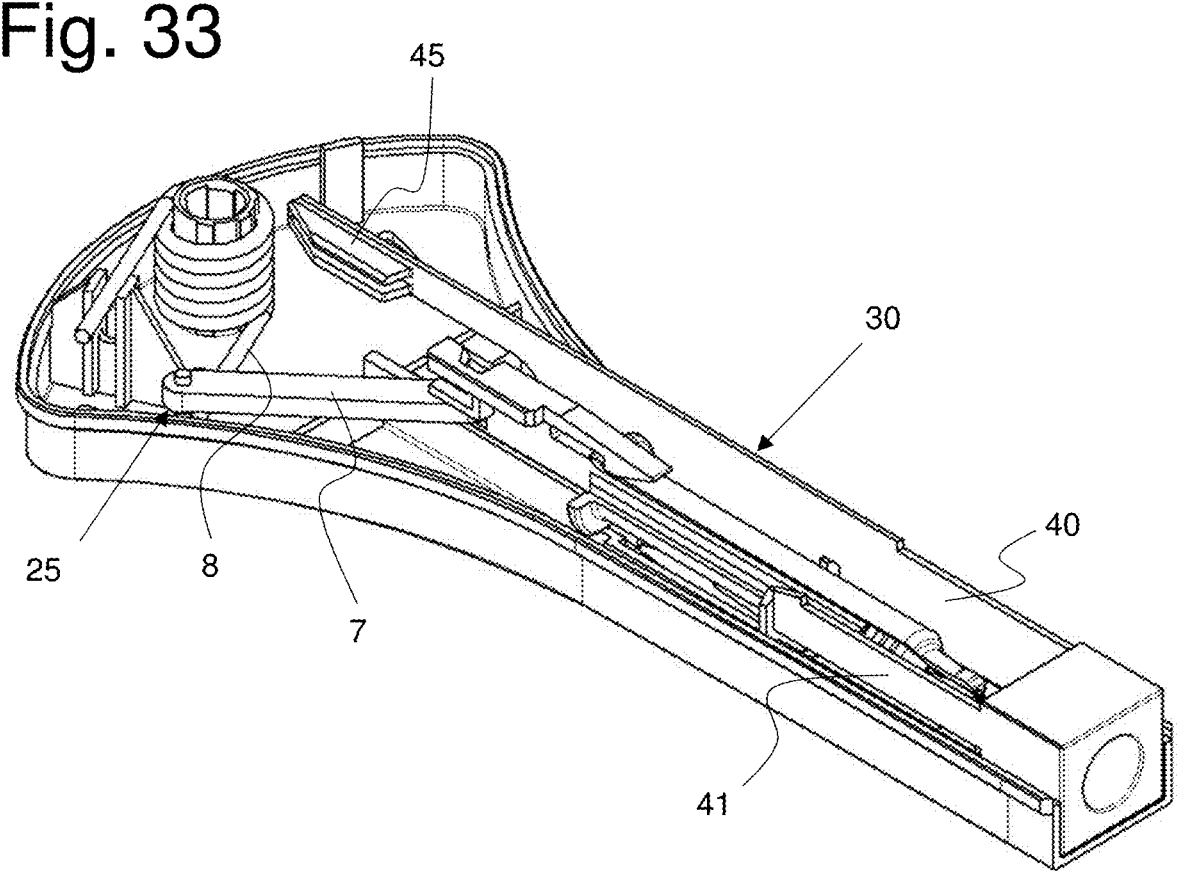
FIG. 33: The self-injector according to FIG. 27 after covering the full spring leg path.

FIG. 29 shows the self-injector after the spring leg 8 has traveled approximately half its travel. In FIG. 30, the spring leg 8 has reached half its pivoting travel. The pivot lever 7 now extends in almost the same direction as the piston movement. In FIG. 31, the spring leg 8 has covered approx. ⅔ of the spring leg travel and the swivel lever 7 is approximately in the direction of movement of the piston. FIG. 32 shows the state when the spring leg 8 has traveled about ¾ of the spring leg path. And finally, FIG. 33 shows the situation when the mobile spring leg 8 has reached its end state at the stop 25, and correspondingly also the pivot lever 7 hinged to it.

Figure 34:
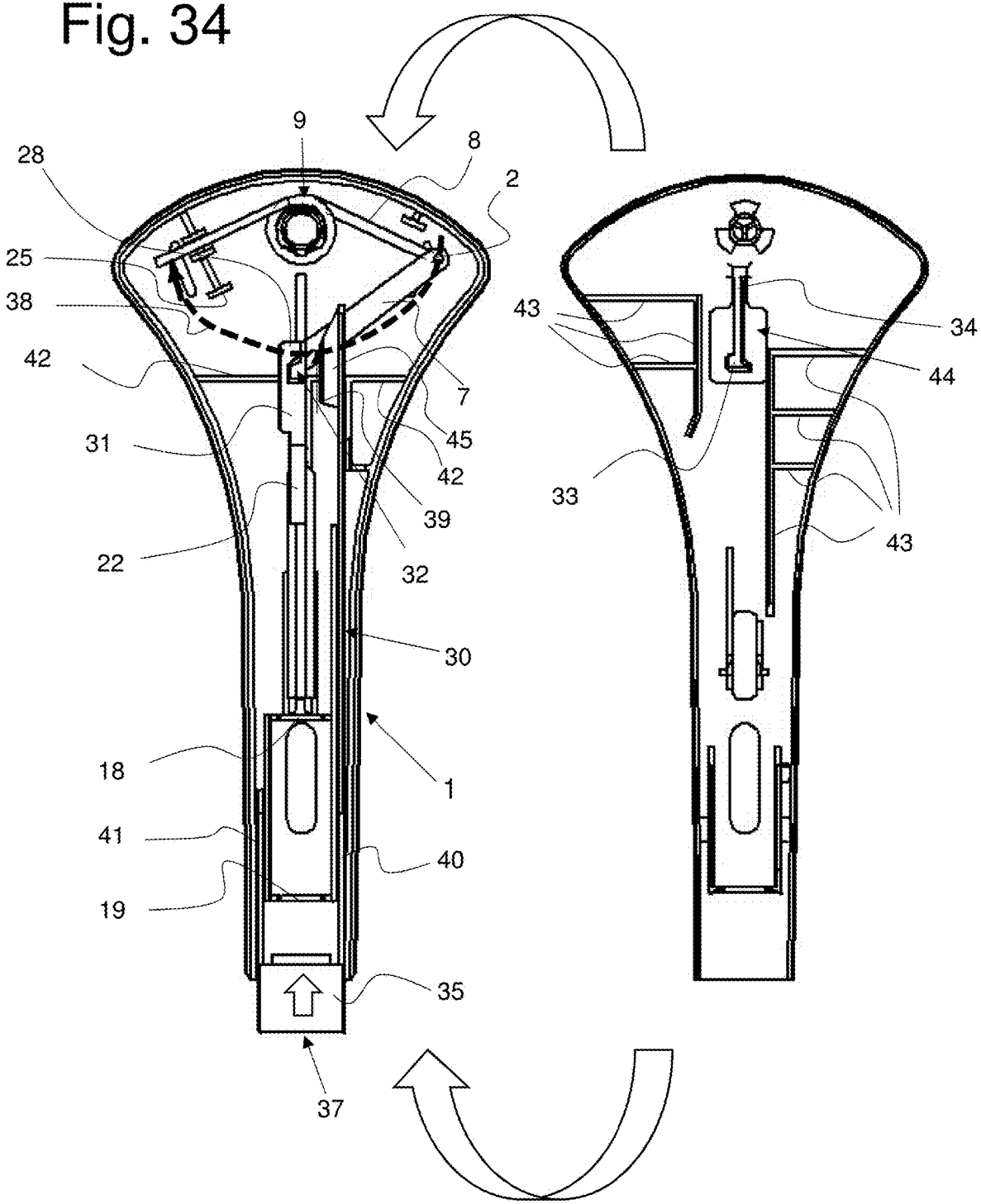
FIG. 34: The two housing parts of the self-injector that click together to illustrate the release mechanism with the displacer for a latch.

Finally, FIG. 34 shows the two housing parts of the self-injector that click together to illustrate its release mechanism, the lower housing part on the left and the upper housing part on the right. In the following, this FIG. 34 is used to describe how the trigger mechanism works in detail. When the syringe is inserted into the self-injector, i.e. on the two bars 18, 19 with their semicircular supports in the lower housing part, the syringe needle 5 projects into the protective chamber 35 and is completely enclosed by it, i.e. does not project out of it, although the protective chamber 35 has a circular hole 37 at the front and is open there. The puller 46 with its tube 47 with its barbs 48 is inserted into this hole 37 and over the push-on cap 27. By pulling it off, the push-on cap 27 with the barbs 48 of the tube 47 can be pulled out of the hole 37 at the front of the protective chamber 35 and removed. The needle still remains concealed in the protective chamber 35. The injection is triggered here by means of a trigger slide 30, which is integrally connected to the front of the protective chamber 35 and terminates at its rear end in a front wedge-shaped displacer 45. When the self-injector is pressed onto the body in the initial state, the protective chamber 35 and thus also the release slide 30 in the housing 1 is pushed backwards into the housing 1 of the self-injector, as indicated by the arrow on the protective chamber 35. The protective chamber 35 moves with ist front hole 37 over the needle tip 5 to the rear, exposing the needle 5 and allowing it to penetrate the skin and muscle. The syringe 3 must now be actuated, i.e. the plunger in the syringe 3 must deliver the active ingredient in the syringe body forwards and through the needle tip into the body.

The release occurs as follows: The upper half of the housing shown here on the right, of which the inside is visible here, is clicked onto the lower housing part shown here on the left, pivoted through 180°, when the self-injector is assembled, as indicated by the two curved arrows. This upper housing part, shown here on the right, has a window or a recess 44 in the rear area, in which an arm 34 is formed which can be elastically pivoted to the left and right and which forms a latch 33 at the front, which in the assembled state projects into a recess 32 on the lower housing part shown on the left, so that it can be seen from the outside, i.e. as seen from above on the upper housing part, when the self-injector is assembled. This is of course not a condition for the function, but merely serves to simplify the production of the moving parts without a slide in the injection mold. When the two housing parts are assembled, this latch 33 presses into the recess 32 in the rear, widened articulation part 31 on the piston slider 22 for the pivoting lever 7 and blocks it, i.e. prevents the piston slider 22 from moving. The pivoting lever 7 can be pivoted with its articulation point 2 at the free end of the movable spring leg 8 along the path shown in dashed lines and is connected to the piston slider 22 in an articulated manner with its other end at the articulation point 28. This can only move forwards along the rail 11 towards the syringe 3, but only when the piston slide 22 is released for a forward movement towards the syringe 3, i.e. when the pawl 33 no longer protrudes into the recess 32 in the articulation part 31 of the piston slide 22. If the protective chamber 35 is now pushed backwards as a result of the syringe being positioned with the release slide 30 formed on it, the wedge-shaped displacer 45 pushes past the elastically pivotable pawl 33 and when its rear edge 39 has passed this pawl 33, it pivots with its inclined surface along the inclined surface on the recess 32 in the housing part from left to right as shown on the left and thus out of the recess 32. The linkage 31 and thus the piston slide 22 are pretensioned by the torsion spring, which acts on the swivel lever 7 and wants to push it forwards towards the syringe. When the pawl 33 slides out of the recess 32 on the articulation part 31, this and thus the piston slide 22 are suddenly released for a longitudinal displacement in the direction of the syringe 3. As a result, the torsion spring 9 with its spring leg 8 can move the pivot lever 7 hinged to it along the dashed semicircular line 38. In the first half of this movement, the piston slide 22 is pushed forcefully towards the syringe 3 and actuates the piston 6 In the second half of the movement, the plunger slide 22 is retracted until the movement of the spring leg 8 and the swivel lever 7 ends with a stop 25. As already described, this second half of the movement pulls the syringe 3 itself a little way back into the housing 1 of the self-injector so that its needle 5 disappears into its housing 1 and can no longer injure anyone. The ribs 44, 42 in the housing parts are intended to reinforce them.

Finally, FIG. 35 shows a special securing plate for mounting this self-injector. For this purpose, the securing plate 49 has a centering cam 50 and a positioning web 51 on the other side. The lower housing part of the housing 1 of the self-injector is designed with corresponding recesses that fit precisely over this centering cam 50 and positioning web 51. This ensures that the locking cam 52 protrudes at the correct position through the lower housing part into the housing 1 and thus blocks the spring leg 8 of the torsion spring. As long as the self-injector rests on this locking plate 49, it cannot be triggered. Only when the self-injector is lifted off this safety plate 49 is it unlocked, so to speak. After removing the puller, it is unlocked and ready for use. By pressing the protective chamber 35 onto the body at the point where the active substance is to be injected, the release slide 30 is pushed into the housing 1, exposing the needle 5 of the syringe and the automatic injection takes place as already described in detail by pushing the plunger 6 in the syringe 3 forwards by means of the torsion spring 9 and then pulling the syringe 3 completely into the interior of the housing 1, causing the needle 5 to disappear into the housing 1. The self-injector is now used, can no longer injure or infect anyone and can be disposed of become.

LIST OF DIGITS

1 Housing
2 Linkage point of spring leg 8 to swivel lever 7/knee joint
3 Syringe
4 Syringe barrel
5 Needle of the syringe
6 Piston
7 Swivel lever
8 Movable leg of the torsion spring
9 Torsion spring
10 Barbs
11 Rail for piston
12 Slide-on lamp at the bottom of the barb
13 rear end of the syringe 3
14 Flange as rear end 13 of the syringe barrel
15 Winding axis Torsion spring
16 Bolt for torsion spring
17 stationary spring leg
18,19 top U-shaped bars
20 Stop for rear end of syringe 3
21 Sloping ramp at the stop 20
22 Piston slide
23 Ramp on piston slide 22
24 Retainer for torsion spring
25 Limiting cams for the swivel range of the movable spring leg
26 Sealing pin at the front of the piston 6
27 Push-on cap for needle 5
28 Pivot point between swivel lever 7 and piston slider 22
29 Legs for access ramp
30 Release slider
31 Linkage part of the piston slide 22
32 Recess for pawl 33 in piston slide 22
33 Release jack
34 Elastic arm for handle 33
35 Protective chamber at the front of the release slide3o
36 Lower edge of the piston slide 22
37 Hole in protective chamber 35
38 Semicircle line of movement
39 Rear edge on displacer 45
40 Slider plate of protective chamber 35 for release slider 30
41 Guide plate on the protective chamber 35 for release slider 30
42 Cross ribs on lower housing section
43 Ribs in the upper part of the housing
44 Window or recess in the upper part of the housing for elastic arm with latch 33
45 Displacer
46 cubic puller
47 Tubes with barbs
48 Barbs in the tube
49 Locking plate
50 Centering cam on locking plate
51 Positioning bar on locking plate
52 Locking cam on locking plate
V Front housing section
H Rear housing section

The invention claimed is:

1. A self-injector with stored energy for application of a contained liquid active substance, the self-injector comprising:
    a housing;
    a holder for holding a syringe to be inserted with a cylinder;
    a piston; and
    a sealing pin and a needle for hydraulically ejecting the liquid active substance through the needle by the piston, the self-injector characterized in that:
        the piston is actuated by a piston slide guided along a rail in the housing by means of a first pivot lever articulated to the piston slide, the actuation of the piston being triggered by a piston sliding plate being pushed into the housing when the self-injector is pressed onto a body surface, an end of the first pivot lever is articulated to a first pivotable spring leg of a prestressed torsion spring having a plurality of coils that is in a pretensioned state, and a second spring leg of the torsion spring stationarily locked to the housing,
    wherein a first pivoting movement of the first pivotable spring leg is triggered by releasing the first pivotable spring leg from the pretensioned state, and
    wherein in a first pivoting phase with the first pivotable spring leg, the piston slide is articulated at the end of first pivotable spring leg, the piston is pushed into the syringe, a barb on the piston slide is latched onto the syringe, and in a subsequent pivoting movement of the first pivotable spring leg with the piston slide, the syringe is withdrawn in the housing.

2. The self-injector according to claim 1, characterized in that:
    the piston is pushed into the cylinder of the syringe by acting on the piston slide, which is guided on the rail which forms a groove-shaped rail in the housing, a barb of a sliding ramp running obliquely to a sliding axis, and a rear end of the syringe includes a flange which projects radially beyond the cylinder and over which the barb is pushed with the sliding ramp elastically and is hooked at an end of the sliding ramp by elastic spring-back, wherein the syringe is retracted within the housing in a second pivoting phase of the first pivot lever until the needle is completely within the housing.

3. The self-injector according to claim 1, characterized in that:
    the piston is operable by the first pivot lever, the first pivot lever is hinged to a rear end of the piston, the torsion spring is mounted with its winding axis on a bolt within the housing and the second spring leg that is stationarily locked to the housing while the first pivotable spring leg is connected in an articulated manner to a rear end of the first pivot lever under tension of the torsion spring, and a front end of the first pivot lever is connected in an articulated manner to a rear end of the piston slide, when the torsion spring, wherein when the first pivot lever can beis pivoted about a point of articulation on the piston slide in a first phase for the syringe until it is located on a displacement axis of the piston, and wherein in a second pivoting phase, when pivoting further, the syringe is retracted into the housing.

4. The self-injector according to claim 1, characterized in that:
the holder for holding the syringe is inserted with the cylinder, the needle has at least two webs which are recessed at a top in a U-shape and into which the cylinder of the syringe fits in a form-fitting manner, and a stop is formed by the housing, against which the syringe abuts with a rear flange of the syringe so that the syringe cannot be displaced into the housing when the needle is inserted into tissue.

5. The self-injector according to claim 1, characterized in that:
the holder for holding the syringe to be inserted with the cylinder and the needle has at least two webs which are recessed in a U-shape manner at a top and into which the cylinder of the syringe fits in a form-fitting manner, and a stop is formed by the housing against which the syringe strikes with its a rear end and flange of the syringe, the stop forming an obliquely sloping ramp in a direction away from the syringe and behind the piston, the piston slide forms a forwardly rising ramp at its lower edge, by means of which it rides, in a final phase of a forward movement, when its barb moves over the rear end and flange of the syringe, onto the obliquely sloping ramp in front of the stop and displaces an elastic leg and the stop located on it, the syringe can subsequently be retracted unobstructedly by the barb into the housing.

6. The self-injector according to claim 1, characterized in that:
the self-injector comprises injection-molded plastic parts with an exception of the needle, the torsion spring and a pertaining puller tube in a puller, which are made of metal.

7. The self-injector according to claim 1, characterized in that:
the housing comprises:
a lower part, which contains all parts for holding and actuating the syringe and its retraction, as well as a trigger slide with a displacer at a front of the trigger slide for triggering, and a congruent upper part of the housing fitting onto the lower part of the housing, the congruent upper part of the housing including a latch formed on an end of an elastically pivotable arm and is laterally flexible, which is clicked congruently onto the lower part.

8. The self-injector according to claim 1, characterized in that:
a trigger slide forms a cubic protective chamber for the needle at a front of the cubic protective chamber and forms a displacer at a rear of the cubic protective chamber for lateral blocking and passing of a trigger latch, and a lateral slide plate and a lateral guide plate located opposite to the lateral slide plate, wherein the trigger slide is guided in the housing parallel to the syringe.

9. The self-injector according to claim 1, characterized in that:
a movement of the piston in the cylinder is ensured in an initial state by pressing a release latch into a recess formed at a rear end of the piston sliding plate, wherein the release latch is elastically pivotable on another part of the housing and is configured to be pushed past the release latch by a displacer formed at a rear end of a sliding rod,
wherein the self-injector further includes a protective chamber positioned at a front of the housing, the protective chamber encloses a tip of the needle on all sides, and
wherein when pressure is applied to the protective chamber when the self-injector is put on, the protective chamber is pushed into the housing pushing the displacer past the release latch, and when a rear edge of the displacer has passed the release latch, the release latch pivots out of the recess of the piston sliding plate and releases the piston sliding plate for a displacement towards the syringe causing the first pivot lever to be pivoted to another side in the housing by means of the torsion spring.

10. The self-injector according to claim 1, characterized in that:
a puller with a metal puller tube with the metal puller tube facing inwards is inserted over a push-on cap of the needle, the push-on cap is released by removing the puller from a housing of the needle of the syringe, while remaining in a protective chamber which forms a front end of the piston sliding plate and pushed back together with the piston sliding plate into the housing for triggering an activation of the self-injector.

11. The self-injector according to claim 1, characterized in that:
in a front part of the housing, into which the syringe is to be inserted, forms a channel which is rectangular in cross-section and a rear part of the housing widens out from this channel in a fan-like manner on both sides and rests on a securing plate so that a locking cam protrudes through a recess in the housing and blocks the first pivotable spring leg of the torsion spring.

* * * * *